(12) United States Patent
Batarseh

(10) Patent No.: US 8,048,870 B2
(45) Date of Patent: Nov. 1, 2011

(54) APOPTOSIS-INDUCING ANTINEOPLASTIC SILVER (I) COORDINATION COMPLEXES

(76) Inventor: Kareem I. Batarseh, Fairfax Station, VA (US)

( * ) Notice: Subject to any disclaimer, the term of this patent is extended or adjusted under 35 U.S.C. 154(b) by 1173 days.

(21) Appl. No.: 11/225,565

(22) Filed: Sep. 13, 2005

(65) Prior Publication Data

US 2006/0154911 A1 Jul. 13, 2006

Related U.S. Application Data

(60) Provisional application No. 60/642,805, filed on Jan. 11, 2005.

(51) Int. Cl.
*A61K 31/33* (2006.01)
(52) U.S. Cl. ........................................ 514/183
(58) Field of Classification Search .................... 514/183
See application file for complete search history.

(56) References Cited

U.S. PATENT DOCUMENTS

| | | | | |
|---|---|---|---|---|
| 4,708,864 A * | 11/1987 | Maurer | | 424/49 |
| 4,915,955 A * | 4/1990 | Gomori | | 424/616 |
| 5,348,950 A | 9/1994 | Hata et al. | | |
| 5,504,055 A * | 4/1996 | Hsu | | 504/121 |
| 6,280,959 B1 | 8/2001 | Gleason et al. | | |
| 6,329,497 B1 * | 12/2001 | Boger | | 530/322 |
| 2002/0136780 A1 * | 9/2002 | Batarseh | | 424/618 |
| 2003/0147970 A1 * | 8/2003 | Newman et al. | | 424/618 |
| 2004/0191329 A1 | 9/2004 | Burrell et al. | | |

FOREIGN PATENT DOCUMENTS

| | | |
|---|---|---|
| JP | 07-138167 | 5/1995 |
| WO | WO 00/62618 | 10/2000 |

OTHER PUBLICATIONS

Coyle et al 'Synthesis, X-ray crystal structure, anti-fungal and anti-cancer activity of [Ag2(NH3)2(salH)2] (salH2 = salicyclic acid)' Journal of Inorganic Biochemistry, vol. 98, p. 1361-1366, 2004.*
Strickley 'Solubilizing Excipients in Oral and Injectable Formulations' Pharmaceutical Research, vol. 21(2), p. 201-229, 2004.*
Bott et al 'Univalent Metal Ion Alpha-Hydroxy Acid Interactions: Part 9. Preparation and Crystal Structures of Lithium Hydrogen (+)-Tartrate monohydrate, Potassium (+)-Tartrate Hemihydrate and Thallium(I) (+)-Tartrate' Polyhedron, 13(22), pp. 3135-3141, 1994.*
Bott et al 'Structures of hydrogen (+)-tartrates of sodium, thallium(I) and silver(I)' Zeitschrift fur Kristallographie, vol. 209, p. 803-807, 1994.*
Batarseh, "Anomaly and correlation of killing in the therapeutic properties of silver (I)-chelation with glutamic and tartaric acids," Journal of Anticrobrial Chemotherapy, vol. 54, No. 2, 2004, pp. 546-548.
Farrell, "Metal Complexes as Drugs and Chemotherapeutic Agents," Kluwer Academic Publishers (Dordrecht and Boston), vol. 11, 1989, pp. 809-840.
International Search Report and Written Opinion of the International Searching Authority for PCT/US06/000390 dated Jul. 27, 2007.
Supplementary European Search Report for corresponding European Patent Application No. 06 71 7569 dated Nov. 20, 2009 (8 pages).
Gil et al., "Carboxilatos hidroxilados de rodio II (gluconato, lactobionato y lactato). Síntesis, caracterización y ensayos de actividad citostática in vitro," Anales De La Real Academia De Farmacia, vol. 66, No. 2, Jan. 1, 2000, pp. 229-239, (see English Summary on pp. 229-230) (11 pages).

* cited by examiner

*Primary Examiner* — Brandon Fetterolf
*Assistant Examiner* — Christopher R Stone

(57) ABSTRACT

The present invention describes chemotherapeutic compositions, a method for making the same, and methods for inducing apoptosis in tumor cells and/or inhibiting tumors. The compositions are metal coordination complexes of a cytotoxic metal, such as silver(I) and a chiral α-organic acid, such as tartaric acid, in a pharmaceutical carrier.

12 Claims, 9 Drawing Sheets

APOPTOSIS-INDUCING ANTINEOPLASTIC SILVER (I) COORDINATION COMPLEXES

This application claims priority under 35 U.S.C. §119(e) of prior U.S. Provisional Patent Application No. 60/642,805 filed Jan. 11, 2005, which is incorporated in its entirety by reference herein.

BACKGROUND OF THE INVENTION

This invention relates to chemotherapeutic agents that are preferably non-lethal, non-corrosive, and/or non-irritating to the recipient, and preferably can cause apoptosis. The present invention can be employed as a chemotherapeutic agent for both solid and disseminated tumors.

The oligodynamic action or the antimicrobial activity of small amounts of metal has been known for a long time and is the basis for the development of many metal coordination complexes therapeutic agents. In fact, metal ions such as mercury (II), cadmium (II), zinc (II), germanium (II), copper (II), and silver (I) ions have been used for the treatment of many infectious diseases (Merluzzi, V. J., et al., *Research Communications in Chemical Path. Pharmacol.*, 66, 425 (1989); Slawson, R. M., et al., *Plasmid*, 27, 72 (1992); Khurshid, H. Pak. *J. Pharmacol.* 13, 41 (1996); Klasen, H. J. *Burns*, 26, 131 (2000); Dibrov, P., et al., *A.A.C.*, 46, 2668 (2002); Richard (III), J. W., et al., *J. Burns and Surg. Wound Care*, 1, 11 (2002)).

Besides the use of heavy metals as antibiotic agents, they are also employed in the design of chemotherapeutic compounds. The current treatments for cell proliferative diseases such as cancer employ metal coordination complexes where such complexes inhibit DNA replication and cell division. The most prominent and promising family of cytotoxic agents that has proved to have clinical benefits is one that uses platinum as the heavy metal (Pil, P., & Lippard, S. in *Encyclopedia of Cancer*, ed. Bertino, J. R. (Academic Press, San Diego), pp. 392-410 (1997); Jakupec, M., et al., *Rev. Physiol. Biochem. Pharmacol.*, 146, 1 (2003)). One of the most active and broad-spectrum chemotherapeutic drugs belonging to this family is cisplatin, cis-diaminedichloroplatinum (II), which is used to treat epithelial malignancies such as testicular cancer and ovarian carcinoma (Pil, P., & Lippard, S. in *Encyclopedia of Cancer*, ed. Bertino, J. R. (Academic Press, San Diego), pp. 392-410 (1997); Jakupec, M., et al., *Rev. Physiol. Biochem. Pharmacol.*, 146, 1 (2003)). Following its serendipitous discovery as an antitumor drug, other useful chemotherapeutic drugs that employ platinum such as carboplatin were also developed (Pil, P., & Lippard, S. in *Encyclopedia of Cancer*, ed. Bertino, J. R. (Academic Press, San Diego), pp. 392-410 (1997)). With this growing interest, other metal coordination complexes have been explored. Examples of such metals are gold, titanium, copper, iridium, and rhodium (Haiduc, I., & Silvestru, C. *In Vivo*, 3, 285 (1989); Caruso, F., et al., *J. Med. Chem.*, 43, 3665-(2000); Caruso, F., et al., *J. Med. Chem.*, 46, 1737 (2003)).

Ionic silver substances are resurging again in popularity due to the fact that silver at low concentrations has no toxicity, mutagenicity or carcinogenic activities, and exhibits an excellent clinical tolerance compared to other metals (Furst, A, & Schlauder, M. *J. Environ. Pathol. Toxicol.*, 1, 51 (1978); Pedahzur, R., et al., *Wat. Sci. Tech.*, 31, 123 (1995); Demerec, M., et al., *Am. Nat.*, 85, 119 (1951); Rossman, T. G., & Molina, M. *Environ. Mutagen.*, 8, 263 (1986); Nishioka, H. *Mutat. Res.*, 31, 185 (1987)). Additionally, ubiquitous metallothioneins, which are present in all living organisms, have the property of binding silver and other metals in metal thiolate cluster structures to transport, store, and detoxify essential and nonessential trace metals that may enter the body (Stillman, M. J., et al., *Metal-Based Drugs*, 1, 375 (1994)).

The quantity of silver administered and its chemical form determine the distribution of silver to various body tissues. Once absorbed, silver undergoes a first-pass effect through the liver, and is secreted into the bile, reducing the systemic distribution to tissues (ATSDR. (1990) Toxicological profile for silver), available online at www$_{dot}$atsdr$_{dot}$cdc$_{dot}$gov/tox-profiles/tp146-p$_{dot}$pdf. The only known condition that results from chronic exposure to high levels of silver for a prolonged period of time in humans is argyria, a benign condition which results in permanent bluish-gray discoloration of the skin. The only clinical effect observed with argyria is an aesthetic effect and there are no pathological changes or inflammatory reactions resulting from silver deposition (IRIS. (1987) Silver.), available online at www$_{dot}$epa$_{dot}$gov/iris/subst/0099$_{dot}$htm. Based on patients receiving i.v. injections of silver arsphenamine, the LOAEL (lowest-observed-adverse-effect level) for argyria was determined to be 0.014 mg/kg/day (IRIS. (1987) Silver. [Online.] www$_{dot}$epa$_{dot}$gov/iris/subst/0099$_{dot}$htm. (The above Internet addresses are altered to substitute "dot" for "." so that the addresses as written are not executable as hyperlinks.)

U.S. patent application Ser. No. 10/867,214, filed Jun. 14, 2004 and incorporated herein in its entirety by reference, describes the use of organo-metallic complexes as chemotherapeutic agents and as anti-microbial agents. The technology described therein relates generally to the combination of two components. The first component is an organic (R) metal (M) complex (R-M), such as described in U.S. Pat. Nos. 6,242,009 and 6,630,172, incorporated in their entirety by reference herein. This R-M complex can be combined with a system for generating one or more reactive oxygen species (ROS) through the agency of reducing cofactors with the combination preferably producing a synergistic effect that can be highly effective in the destruction of microbes and/or cancerous or pre-cancerous cells. The composition can be prepared by mixing a metal salt compound in an aqueous solution, and an inorganic acid at room temperature to adjust the pH of the solution; adding an amino acid or potassium sodium tartrate in a specified amount with respect to the valency of the designated metal while homogenizing the mixture, and adding a ROS generating system. Depending on its use, the resultant solution can then be used either directly, or can be diluted with aqueous solutions such as distilled and/or deionized water to provide the necessary cytotoxicity and biocidal activities. The invention of U.S. patent application Ser. No. 10/867,214 can be prepared in any manner that produces an R-M complex in combination with an ROS. More specifically, the cited invention can be prepared by first preparing the R-M complex in any method described in U.S. Pat. Nos. 6,242,009 and 6,630,172, incorporated in their entirety by reference herein. The R part of the complex represents an amino acid such as isoleucine, phenylalanine, leucine, lysine, methionine, threonine, tryptophan, valine, alanine, glycine, arginine, histidine, asparagine, aspartic acid, cysteine, glutamic acid, glutamine, phenylalanine, proline, serine, tyrosine, or mixtures thereof or potassium sodium tartrate. With respect to the other part of the complex that is M, M represents at least one monovalent or polyvalent metal ion or cation, which is anticancerous and/or antimicrobial to at least one microorganism. Preferably, the metal ion is anticancerous and/or microbicidal to a multitude of microorganisms. Examples of the metal ion include, but are not limited to, cations of silver including colloidal silver, copper, zinc, mercury, manganese, chromium, nickel, cadmium, arsenic, cobalt, aluminum, lead, iron, rhodium, iridium, selenium, platinum, gold, titanium, tin, barium, bismuth, vanadium, iron, strontium, antimony, and salts thereof, and the like, and any combination thereof.

The rate of formation of ROS can be allowed to proceed unassisted or may be enhanced through the use of rate increasing agents, like compounds such as enzymes/co-enzymes or catalysts/co-factors. Generally, a coenzyme can contact and reduce a metal catalyst. The reduced metal catalyst may then function to facilitate the production of ROS from the ROS generating species, ordinarily through the donation of an electron. Any number of reducing cofactors/coenzymes may be used. More specifically, the coenzymes (reduced form shown), nicotinamide adenine dinucleotide (NADH), nicotinamide adenine dinucleotide phosphate (NADPH) and/or flavin adenine dinucleotide (FADH) are particularly effective as electron carriers. Similarly, any number of oxidizing metal catalysts/cofactors capable of generating ROS can be utilized. More specifically, $Cu^{2+}$, $Fe^{2+}$, $Fe^{3+}$, $K^+$, $Mg^{2+}$, $Mn^{2+}$, Mo, $Ni^{2+}$, Se, and/or $Zn^{2+}$ are particularly effective catalysts. These catalysts may be used in their pure form or may be combined with a salt and then be introduced into a solvent. One method of producing ROS can be through the breakdown of $H_2O_2$ (hydrogen peroxide) to form hydroxyl radicals.

The current treatments for cancer employ cytotoxic heavy metals, which inhibit cell division and DNA replication. Albeit various robust methods and techniques have been employed to combat cancer, there is a deluge of caveats and various difficulties associated with cancer therapy. Cancer therapy nowadays involves a multi-modality approach of a combination of chemotherapy, radiation, hormone therapy, immunotherapy, and antiangiogenic drugs. Surgery, on the other hand, involves the bulk removal of diseased tissue. While surgery is sometimes effective in removing solid tumors located at certain sites, for example, in the breast, colon, and skin, it cannot be used in the treatment of tumors located in other areas, such as the backbone, nor in the treatment of disseminated neoplastic conditions such as leukemia. If portions of the primary tumor cannot be removed or if it is believed to have metastasized, systemic drug therapy is given to kill residual cancerous cells through targeting of actively dividing cells.

There are difficulties associated with metal-based cancerous compounds in that effective treatment is hampered by lack of specificity and difficulty in delivering these agents to the site of the carcinogenic tumors. The lack of specificity of cytotoxic drugs for tumors cells and the resulting toxicity to normal tissue hampers an additional exploitation of their apoptotic effects. This is especially true with using hemotherapeutic and cytotoxic agents with solid neoplasms since within the inter region of neoplasmic cells, the network of blood capillaries is too small for such agents to be delivered (Jain, R. K. *Cancer Metastasis Rev.*, 9, 253 (1990); Forbes, N. S., et al., *Cancer Res.*, 63, 5188 (2003); Znati, C. A., et al., *Clin. Cancer Res.*, 9, 5508 (2003); Jain, R. K. *Nat. Med.*, 9, 685 (2003); Jain, R., & Booth, M. F. *J. Clin. Invest.*, 112, 1134 (2003); Jain, R. K. in *Clinical Oncology*, eds. Abeloff, M., Armtage, J., Niederhuber, J., Kastan, M., McKenna, W., 3rd ed., (Elsevier, Philadelphia), pp. 153-172 (2004)). These regions commonly exist in most major classes of solid tumors such as those associated with breast, head and neck, pancreatic, stomach, ovarian, cervical, lung, and prostate tumors.

Adding to that is the problem of the patient developing a resistance with the continual, prolonged use of such agents. There is also a plethora of adverse side effects, some of which are irreversible, associated with cisplatin, including tubular necrosis, thrombocytopenia, anaemia, nausea, tinnitus, loss of sight, peripheral and autonomic neuropathies, urticaria, erythema, facial oedema, cytopenia, cachexia, alopecia, and angioedema, and many others related to pulmonary, reproductive and endocrine, and even cardiac arrest, especially at high doses (Slapak, C. A., & Kufe, D. W. in *Harrison's Principles of Internal Medicine*, ed. Isselbacker, K. J., 14th ed., (McGraw-Hill, New York), pp. 523-537 (1998); Sweetman, S. C. *Martindale: the Complete Drug Reference*, 3rd ed., (Pharmaceutical Press, London-Chicago), pp. 525-527 (2002)). These induced side effects significantly impact the quality of life of the patient and frequently dramatically influence the patient's compliance with the treatment regimen. These complications are the major dose-limiting toxicity and can lead to hospitalization of the patient and analgesics for the alleviation of pain.

In addition, new approaches are needed to overcome the two major overriding problems in the design of chemotherapeutic drugs; namely, the lack of selectivity of chemotherapeutic drugs in distinguishing normal and tumor cells, and the common occurrence of drug-resistant tumors. Cytotoxic drugs select only those cells that are able to withstand assault, while resistant cells remain unaffected. This as a result will eliminate the complete clinical effectiveness of the designated drug. Given the current state of affairs, there is an immediate need to develop cytotoxic drugs that can circumvent these obstacles. Therefore, central tenets in the design of such molecules are the control of toxicity and targeting of the metal to specific cancerous cells.

Accordingly, there is an immediate need to develop and design a new generation of chemotherapeutic agents that are able to overcome the above-described disadvantages.

SUMMARY OF THE INVENTION

In accordance with the present invention, new compositions and methods are provided for inducing apoptosis in tumor cells and for treating an animal afflicted with a tumor. In one broad aspect, the present invention relates to a composition comprising a metal coordination complex of at least one cytotoxic metal and at least one chiral α-organic acid in a pharmaceutical carrier. This aspect of the present invention may further encompass the following specific, non-limiting features: The cytotoxic metal may be silver, platinum, germanium, gallium, ruthenium, osmium, rhodium, iridium or mixtures thereof. The chiral α-organic acid may be tartaric acid, malic acid or lactic acid, and in particular, may be tartaric acid, or more specifically, L-(+)-tartaric acid or (2R, 3R)-(+)-tartaric acid.

In another broad aspect, the present invention relates to a composition comprising a silver(I)-chiral α-organic acid coordination complex in a pharmaceutical carrier. This aspect of the present invention may further encompass the following specific, non-limiting features: The metal coordination complex may be formed by combining at least one inorganic acid, at least one surfactant, at least one chiral α-organic acid, and at least one metal salt in an aqueous solvent and may be formed at pH conditions of pH 2.0 or less. The amount of surfactant that is present in the aqueous solvent may be no greater than an equimolar portion with respect to the amount of the cytotoxic metal. The amount of chiral α-organic acid that is present in the aqueous solvent may be no greater than four times the equimolar portion with respect to the amount of cytotoxic metal. The surfactant may be an ionic surfactant or a nonionic surfactant and, for example, may be sodium tripolyphosphate. The inorganic acid, for example, can be phosphoric acid. The metal coordination complex may formed by first adding the inorganic acid to the aqueous solvent, then adding the surfactant, then adding the chiral α-organic acid and then adding the metal salt. The silver(I) of the silver(I)-chiral α-organic acid coordination complex may be in non-colloidal form or may be in colloidal form. The chiral α-organic acid may be tartaric acid, malic acid or lactic acid, and in particular, may be tartaric acid, or more specifically, L-(+)-tartaric acid or (2R,3R)-(+)-tartaric acid. The composition may further contain at least one amino acid. More specifically, the composition may further contain at least one amino acid selected from, for instance, isoleucine, phenylalanine, leucine, lysine, methionine, threonine, tryptophan, valine, alanine, glycine, arginine, histidine, hydroxyproline, gamma-aminobutyric acid, asparagine, aspartic acid, cysteine, glutamic acid, glutamine, phenylalanine, proline, serine, tyrosine, or mixtures thereof. Even more specifically, the composition may further contain glutamic acid. The composition may also contain at least one DNA-intercalating agent and/or at least one angiogenesis inhibitory agent.

In another broad aspect, the present invention relates to a method of inducing apoptosis in tumor cells and/or a method of inhibiting the growth of tumor cells in a mammal, the method comprising administering or contacting the tumor cells with a composition containing at least one metal coordination complex of a cytotoxic metal and at least one chiral α-organic acid. This aspect of the present invention may further encompass the following specific, non-limiting features: The chiral α-organic acid may be, for example, tartaric acid, malic acid, lactic acid or mixtures thereof and in particular, may be tartaric acid, or more specifically, L-(+)-tartaric acid or (2R,3R)-(+)-tartaric acid. The cytotoxic metal may be silver, platinum, germanium, gallium, ruthenium, osmium, rhodium, iridium or mixtures thereof, and in particular, may be silver(I). The composition used in the method may further contain additional ingredients, such as at least one amino acid that enhances silver coordination, such as, for example, isoleucine, phenylalanine, leucine, lysine, methionine, threonine, tryptophan, valine, alanine, glycine, arginine, histidine, hydroxyproline, gamma-aminobutyric acid, asparagine, aspartic acid, cysteine, glutamic acid, glutamine, phenylalanine, proline, serine, tyrosine, and mixtures thereof, and for example, the composition may further contain glutamic acid.

In another broad aspect, the present invention relates to a method of inducing apoptosis in tumor cells and/or a method of inhibiting the growth of tumor cells in a mammal, the method comprising administering to the mammal an effective amount of a composition containing at least one silver (I) coordination complex comprising ionic silver and at least one chiral α-organic acid. This aspect of the present invention may further encompass the following specific, non-limiting features: The chiral α-organic acid may be tartaric acid, malic acid, lactic acid or mixtures thereof and in particular, may be tartaric acid, or more specifically, L-(+)-tartaric acid or (2R,3R)-(+)-tartaric acid. The composition used in the method may further contain additional ingredients, such as at least one amino acid that enhances silver coordination, such as, for example, isoleucine, phenylalanine, leucine, lysine, methionine, threonine, tryptophan, valine, alanine, glycine, arginine, histidine, hydroxyproline, gamma-aminobutyric acid, asparagine, aspartic acid, cysteine, glutamic acid, glutamine, phenylalanine, proline, serine, tyrosine, or mixtures thereof, and, for example, the composition may further contain glutamic acid. As a specific, non-limiting example, if glutamic acid is used in the preparation of the complex, the composition may be administered to a mammal so that the tumor cells are exposed to a concentration of silver in the silver (I) coordination complex of less than about 0.488 µg/ml or more than about 15.625 µg/ml. As a specific, non-limiting example, if glutamic acid is not used in the preparation of the complex, the composition may be administered to a mammal so that the tumor cells are exposed to a concentration of silver in the silver (I) coordination complex of more than about 3.906 µg/ml.

In another broad aspect, the present invention relates to a method of making a silver(I) chiral α-organic acid coordination complex comprising the steps of (a) adding at least one inorganic acid to an aqueous solvent to provide a solution having a pH of 2.0 or less, then (b) adding a surfactant to the solution after step (a), then (c) adding at least one chiral α-organic acid to the solution after step (b) and then (d) adding a silver(I) salt to the solution after step (c), whereby the chiral α-organic acid and silver (I) from the silver(I) salt interact to form the silver(I) chiral α-organic acid complex. This aspect of the present invention may further encompass the following specific, non-limiting features: The amount of surfactant that is present in the aqueous solvent may be preferably no greater than an equimolar portion with respect to the amount of silver(I) present. The amount of chiral α-organic acid that is present in the aqueous solvent may be preferably no greater than four times the equimolar portion with respect to the amount of silver(I) present. The surfactant may be an ionic surfactant or a nonionic surfactant and, in particular, may be sodium tripolyphosphate. The inorganic acid may be phosphoric acid. The chiral α-organic acid may be tartaric acid, malic acid, lactic acid or mixtures thereof and in particular, may be tartaric acid, or more specifically, L-(+)-tartaric acid or (2R,3R)-(+)-tartaric acid. The silver(I) salt is silver nitrate.

In another broad aspect, since silver undergoes a first-pass effect through the liver, and is secreted into the bile (ATSDR. (1990) Toxicological profile for silver), available online at www$_{dot}$atsdr$_{dot}$cdc$_{dot}$gov/toxprofiles/tp146-p$_{dot}$pdf, the present invention can be used for the treatment of all types of hepatitis.

Additional features and advantages of the present invention will be set forth in part in the description that follows, and in part will be apparent from the description, or may be learned by practice of the present invention. The objectives and other advantages of the present invention will be realized and attained by means of the elements and combinations particularly pointed out in the description and appended claims.

It is to be understood that the preceding general discussion and the discussion which follows are considered explanatory and exemplary in nature, and are solely intended to give additional merits of the current invention, as claimed.

DETAILED DESCRIPTION OF THE INVENTION

Figure 1:
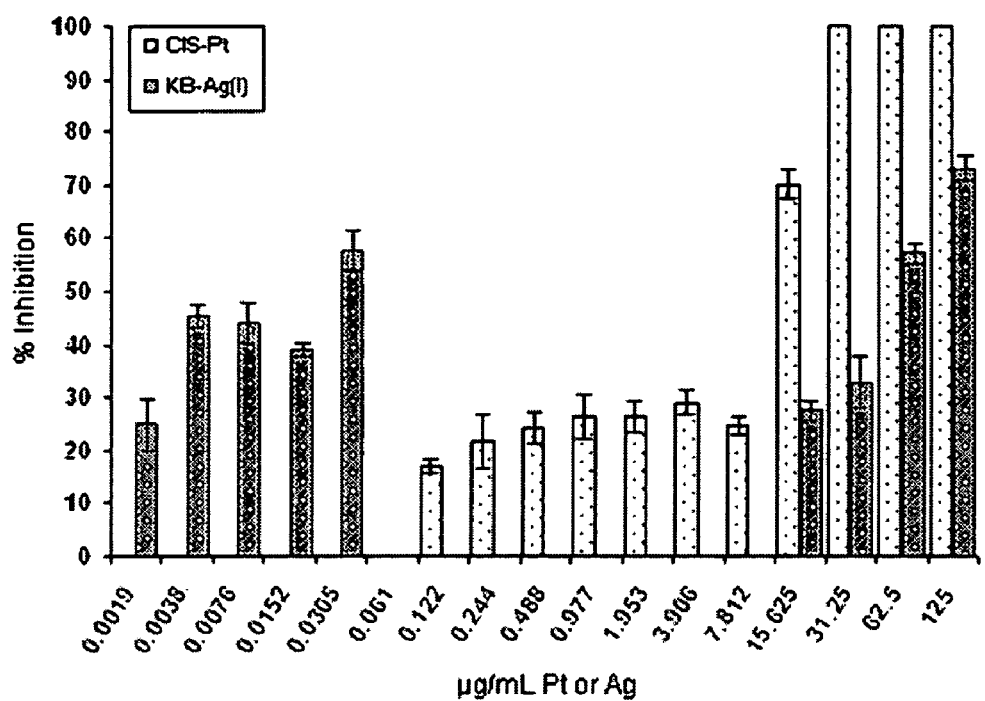
FIG. 1 is a chart illustrating the % inhibition of cisplatin (CIS-Pt) and silver (1) complex (KB-Ag(I)) for T-47D.

The present invention relates generally to the formation of inorganic silver (I) coordination complexes where organic acids or salts thereof can form coordinate bonds to the central silver (I) atom. These complexes can be highly effective as chemotherapeutic drugs, which are highly effective in the destruction of cancerous or pre-cancerous cells, originating from solid and disseminated tumors. The mechanism of cytotoxicity is preferably via apoptosis, which occurs when the genetic checkpoints of the cell cycle machinery is compromised, resulting in shrinkage of cells, membrane blebbing, degradation of chromatin and its dissolution (karyolysis), nuclear condensation, internucleosomal DNA fragmentation, mitochondrial break-down with the release of cytochrome c, which is a pivotal in the activation of the caspase cascade, or cytoskeletal cell disruption and breakage into small, membrane-wrapped, fragments (Darzynkiewicz, Z., et al., *Hum. Cell*, 1, 3 (1998); Ferreira, C., et al., *Clin. Cancer Res.*, 8, 2024 (2002)).

In general, the present invention depends on the formation of inorganic silver (I) coordination complexes that employs asymmetric or chiral alpha(α)-organic acids where the hydroxyl group (—OH) is present on the carbon atom immediately adjacent to the carboxylic acid group (—COOH), having the general structure R—CHOH—COO(Ag), where R represents an alkyl group. By definition, asymmetric or chiral molecules are those molecules that contain an $sp^3$ hybridized carbon atom attached to four different groups. The inorganic silver (I) coordination complex is formed from an aqueous milieu such as distilled-deionized water, an inorganic acid such as phosphoric acid, a surfactant such as sodium tripolyphosphate, a chiral α-organic acid such as tartaric acid and a silver (I) salt such as silver nitrate. This mixture can be added to aqueous solutions to form suitable chemotherapeutic drugs.

The amounts of the surfactant and chiral α-organic acid used in the preparation of the solution can vary, depending on the surfactant and chiral α-organic acid being used. Preferably, not more than equal (1.0) and four (4.0) times the equimolar portion of the surfactant and chiral α-organic acid with respect to silver (I) should be used, respectively, and at least one tenth (0.1) and one and a half (1.5) times the stoichiometric amount of silver (I), respectively.

The inorganic silver (I) coordination complex of the present invention is preferably accomplished by forming the complex under low pH conditions (e.g., acidic conditions) and preferably at pH conditions of pH 2.0 or less.

The inorganic silver (I) coordination complex containing a chemotherapeutic formulation can be prepared with at least one inorganic acid in an aqueous medium, then adding the surfactant and the chiral α-organic acid in their designated amounts, and finally dissolving a silver (I) salt. The composition provided here may be prepared from various complexes that may form together a more complicated complex and/or complexes. The amount of surfactant and chiral α-organic acid used in the preparation of the inorganic silver (I) coordination complex can vary. Preferably, not more than equal (1.0) and four (4.0) times the equimolar portion of the surfactant and chiral α-organic acid with respect to silver (I) is preferably used, respectively. Any source of silver (I), such as in the form of salts, can be used in the present invention. Colloidal silver can be used as well.

Silver is preferably used for the preparation of the present invention. Nonetheless, other metals that are known to exhibit cytotoxic activities can be used as well such as platinum, germanium, gallium, ruthenium, osmium, rhodium, iridium, and mixtures thereof and the like.

The inorganic silver (I) coordination complex of the present invention can preferably be prepared from at least one inorganic acid, a surfactant, a chiral α-organic acid, and one silver salt compound. In a preferred process of making the inorganic silver (I) coordination complex of the present invention, an inorganic acid is added preferably in the presence of an aqueous solvent like a distilled-deionized water, adding to this solution a surfactant, a chiral α-organic acid, a silver salt at room temperature (e.g., 20-30 degree C.), and preferably while homogenizing the mixture. This preparation preferably occurs under low pH conditions, such as a pH of about 2.0 or less. The resulting solution can then be further diluted with aqueous solution or other additives can be added to form the chemotherapeutic compositions of the present invention. Examples of such aqueous solutions are phosphate buffered saline solution (PBS), dimethyl sulfoxide (DMSO), or any other physiological buffer solutions that are commonly used in the pharmaceutical industry, which are preferably approved for such uses to form the chemotherapeutic compositions of the present invention. Preferably, the sequence of addition of chemical compositions to the aqueous medium is conducted in the manner described above, that is, the inorganic acid followed by the surfactant, the chiral α-organic acid, and finally the silver salt, and the mixing is done gently, in order to reduce the risk of precipitation of silver from the solution, precluding its chemotherapeutic effectiveness. Other orders of addition can be used.

With respect to the inorganic acid, any inorganic acid can be used. Preferably, the inorganic acid is phosphoric acid or the like. More than one inorganic acid can be used. As for the surfactants, any ionic and nonionic surfactants can be used. It is contemplated that such surfactants that are considered harmless, such as those found in the pharmaceutical industry, such as, for example, sodium tripolyphosphate and the like, may be used.

Any one or more chiral α-organic acid(s) can be used. Preferably, examples of chiral α-organic acid that can be used include, but are not limited to, tartaric acid, malic acid, lactic acid, and derivatives thereof and mixtures thereof.

Additionally, amino acids can be added to enhance silver coordination. Examples of amino acids include, but are not limited to, alpha-amino acids such as, isoleucine, phenylalanine, leucine, lysine, methionine, threonine, tryptophan, valine, alanine, glycine, arginine, histidine, hydroxyproline, gamma-aminobutyric acid, asparagine, aspartic acid, cysteine, glutamic acid, glutamine, phenylalanine, proline, serine, tyrosine, and derivatives thereof and mixtures thereof.

Several DNA-intercalating agents can be added as well, such as those associated with the ability to poison the enzymes topoisomerase I and topoisomerase II, which are responsible for the interconversion of the topological states during DNA transcription and replication, and the regulation of DNA supercoiling. Examples of topoisomerase I poisons include protoberberines alkaloids and their synthetic analogs, coralyne, the benzo[c]phenanthridine alkaloids, nitidine (LaVoie, E. J., et al., The Second Monroe Wall Symposium on Biodiversity, Natural Product Discovery and Biotechnology, Simon Bolivar University, Caracas, Venezuela, Jan. 7-9 (1998); Makhey et al., *Bioorg. & Med. Chem.*, 4, 781 (1996); Makhey et al., *Med. Chem. Res.*, 5, 1(1995); and Janin et al., *J. Med. Chem.*, 18, 708 (1975)), as well as the fungal metabolites, bulgarein (Fujii et al., *J. Biol. Chem.*, 268, 13160 (1993)), camptothecin and its derivatives, such as topotecan and irinotecan, bi- and terbenzimidazoles (Bailly, C., *CMC*, 7, No. 1, 39 (2000); Kim et al., *J. Med. Chem.* 1996, 39, 992 (1996); Sun et al., *J. Med. Chem.* 1995, 38, 3638 (1995); and Chen et al., *Cancer Res.*, 53, 1332 (1993)), indolocarbazole derivatives (Bailly, C., *CMC*, 7, No. 1, 39 (2000); and Yamashita et al., *Biochemistry*, 31, 12069 (1992)), and saintopin (Yamashita et al., *Biochemistry*, 30, 5838 (1991)). Other topoisomerase I poisons are β-lapachone, diospyrin, topostatin, topostin, flavonoids, Hoechst 33258 and the like and mixtures thereof. Examples of topoisomerase II poisons include teniposide or epipodophyllotoxin, VP-16 and VM-26, and podophyllotoxin-acridine conjugates-pACR6 and pACR8 (Rothenborg-Jensen et al., *Anti-Cancer Drug Design*, 16, 305 (2001)), and the like and mixtures thereof.

Certain embodiments of the present invention can include angiogenesis inhibitory drugs such as angiostatin (O'Reilly, M., et al., *Cell*, 79, 315 (1994)) and endostatin (O'Reilly, M., et al., *Cell*, 88, 1 (1997)), or mixtures thereof, for instance, in conventional amounts.

The compositions can be bottled or packaged via a variety of types of dispensers to further facilitate its usefulness. Other forms of packaging can be readily apparent to those skilled in the art. With respect to the material of packing, such material should preferably be made of opaque glass containers.

It will be apparent to those skilled in the art that the complexes described herein can be administered via controlled release metering devices. The methods and devices include biodegradable polymers, liposomes, sugars, hormones, antibodies, syringes, infusion devices, and the like.

In still another preferred embodiment of the present invention, the compositions are nontoxic, nonirritant, and/or noncorrosive, while possessing cytotoxicity against both solid and disseminated tumors.

The resulting solution can then be further diluted with an aqueous solution, and preferably, phosphate buffered saline solutions (PBS), dimethyl sulfoxide (DMSO) or any other physiological buffer solution that is commonly used in the pharmaceutical industry, which are approved for such uses to form the chemotherapeutic compositions of the present invention. The compositions of the present invention may be conveniently provided in a liquid carrier. Any liquid carrier may be employed provided that such carrier should behave as an inert, that is, should not chemically interfere with the chemical constituents of the composition. Other delivery routes will be readily apparent to those skilled in the art.

The present compositions are safely given to subjects via intradermal, intramuscular, intravenous (i.v.), or intraperitoneal (i.p.) injections or any other effective route to the site of the tumor. Preferably, the route of administration is designed to obtain direct contact with the condition(s) being treated. The compositions can further contain pharmaceutically acceptable stabilizers, adjuvants, diluents, bioactive chemicals such as antivirals, antibiotics or mixtures thereof, and other components that are well known to those skilled in the art, and other ingredients commonly used in the pharmaceutical industry, which are approved for such uses. Again, such carriers should act as inert.

In another embodiment, the present invention can be stored in a non-reactive state, and activation of the disclosed compositions can then be done by the user at the site of application.

The term "chemotherapeutic" as used herein can be considered as the inhibition of the growth of cancer cells that are sensitive to the compositions disclosed herein, via therapy involving the administration of an effective amount of the subject invention. Preferably, such treatment also leads to some regression of cancerous cells. Most preferably, such treatment leads to the near complete or complete regression of cancerous cells. The term "cytotoxic" as used herein is considered to be the degree to which something is toxic to living cells.

The concentrations of the present invention depend on many factors, including site of treatment, the desired response and duration of the composition's action, and other factors that will be apparent to those skilled in the art.

The present invention is further illustrated by the following representative and non-limiting examples. These experiments constitute some of the embodiments of the invention disclosed herein. The main impetus behind these examples is solely for the purpose of illustration and is in no way of limitation.

Methodology

Chemicals

Sterile, double-distilled-deionized water was used for all cytotoxic assays and for the preparation of Ag solutions and complexes. Pharmaceutical-grade reagents were purchased from Sigma-Aldrich while a vial of 100 mL, containing 50 mg cisplatin "Ebewe" as active ingredient was purchased from EBEWE Arzneimittel Ges.m.b.H Laboratories (Unterach, Austria).

Tumor Cell Lines

The chemotherapeutic activities of the silver (I) coordination complex were determined on T-47D human breast carcinoma and Jurkat T-cell acute lymphoblastic leukemia, and compared with cisplatin ($Pt(NH_3)_2Cl_2$) at 385 µg/mL, corresponding to 250 µg/mL platinum, which is the same concentration used for Ag for the experiments described in Examples 1 and 2, below. The two tumor cell lines were chosen very carefully so as to include solid (T-47D) and disseminated (Jurkat) neoplasia. Cells are plated in a 96-well flat bottom tissue culture plates at 50,000 cells/well. The experiments were conducted by serial dilution.

All cell lines were grown and tested in complete RPMI-1640 medium supplemented with 10% FBS, 40 µg/mL GEN, HEPES buffer of pH=7.2, 2 mM L-glutamine and sodium pyruvate. Plates were incubated in 5% $CO_2$ at 37° C. in a humidified incubator for 24 hrs. Human tumor cells were maintained in the log phase by routine passaging every 2-3 days.

Assessment of Cytotoxicity

To assess % inhibition of tumor cells, the number of viable cells were counted by trypan blue dye exclusion method on a hemocytometer by microscopy, and adjusted for concentration of cells/mL. Briefly, each well was plated and washed with PBS twice and then harvested with 0.5 mL of Trypsin/EDTA. Cells were diluted with 1 ml of culture media and stained with trypan blue dye.

To examine if there was any interaction between culture medium and test reagents, the test culture was also inoculated with the present reagents without the presence of any of the drugs. All controls turned out as expected, validating the observations of the actual experiments. All experiments were done in triplicates, and the results are averaged and reported.

Detection of Apoptosis

Detection of in-situ apoptosis was performed by the DeadEnd Colorimetric TUNEL (terminal deoxynucleotidyltransferase nick end labeling) assay for the detection of apoptosis in cultured cells as described in Promega kit (Promega Corporation-2800 Woods Hollow Road, Madison, Wis. 53711-5399, USA). Briefly, control and apoptosis-induced cells were centrifuged, washed with PBS, and were fixed on glass slides coated with poly-$_L$-lysine (Sigma-Aldrich). The cells were fixed by immersing the slides in 10% buffered formalin, 4% paraformaldehyde solution for 25 minutes at room temperature. The fixed cells were then washed twice with fresh PBS for 5 minutes at room temperature. The cells were permeabilized by immersing the slides in 0.2% Triton® X-100 solution in PBS for 5 minutes at room temperature. The slides were then rinsed twice with PBS for 5 minutes each at room temperature. The excess liquid was then removed by tapping the slides, and the cells were covered with 100 µL of Equilibration Buffer, and the slides were equilibrated for 8 minutes at room temperature. Then, 100 µL of rTdT reaction mix were added and blotted around the equilibrated areas. The slides were then incubated at 37° C. for an hour inside a humidifier. Then, the reactions were terminated, the slides were washed and 0.3% hydrogen peroxide, and other reagents and washing steps were conducted according to the manufacturer's instructions. The slides were then observed under a light microscope for apoptotic staining. For comparative purposes, apoptotic studies were also performed on cisplatin. Positive and negative controls were employed by using methotrexate (MTX), and by maintaining the cells in the media without any cytotoxic drugs (NEG), respectively.

Molecular Structure, Thermal and Thermogravimetric Properties, and Purity

The structural, thermal and thermogravimetric measurements of the complex were determined by X-ray Crystallography (XRC), Differential Scanning Calorimetry (DSC) and Thermogravimetry (TG), respectively. These measurements were conducted by a professional laboratory, Chemir Analytical Services (2672 Metro Blvd., Maryland Heights, Mo. 63043-USA; www$_{dot}$chemir$_{dot}$com). The structure has been further confirmed by Dr. Peter Y. Zavalij (Director, X-ray Crystallographic Laboratory: Department of Chemistry & Biochemistry, 091 Chemistry Building, University of Maryland—College Park, Md. 20742-4454). The purity criterion of the complex for carbon and hydrogen was determined by combustion/gravimetric method while for silver by standard atomic absorption.

Single-crystal XRC was carried out on a Bruker SMART 1000 CCD diffractometer. A colorless single prismatic crystal with approximate dimensions 0.23×0.2×0.18 mm$^3$ was mounted, aligned and diffraction patterns were collected. The X-ray intensity data were measured at 170(2) K on a Bruker SMART 1000 CCD diffractometer using a graphite monochromator and a MoKα fine-focus sealed tube (λ=0.71073 Å), and unit cell dimension was obtained with least-squares refinements. The assignment of silver atom to the single high-electron-density atom allowed phasing of the data set. The space group, unit cell dimensions, and other parameters were determined. The refined structure yielded bond lengths and angles, atomic coordinates, and anisotropic parameters. The program SAINT was used for integration of the diffraction patterns, while the structure was solved by direct SHELXS-plus program (SMART and SHELXTL-plus Software. Brucker AXS Inc. Madison, Wis., USA). All non-hydrogen atoms were located in successive difference Fourier analyses. The final refinement was done by full matrix least-squares analyses with anisotropic thermal parameters for non-hydrogen atoms on F$^2$. Hydrogen atoms bounded to oxygen were located from a difference Fourier map, while others were placed theoretically, riding on the concerned atom and refined with a common isotropic displacement parameter.

DSC measurements were performed with a Perkin-Elmer/DSC Series 7 using a scan temperature range of 25-300° C. at a heating rate of 10° C./min, and a sample weight of 5.4 mg. TG measurements were performed with a Perkin-Elmer TGA 7 with TAC 7/DX controller using a scan temperature range of 25-600° C., a heating rate of 20° C./min with a sample weight of 11.872 mg.

EXAMPLE 1

Preparation of Silver (I) Coordination Complex (KB-Ag(I))

At room temperature, and under minimum light, 0.5 ml of 85% H$_3$PO$_4$ was added to 4.0 ml of doubled distilled deionized water. To that, 0.2 g of sodium tripolyphosphate was added while mixing, followed by 1.94 g of L-(+)-tartaric acid or (2R,3R)-(+)-tartaric acid. The resultant solution was stirred gently until homogenization was achieved. Then, 0.7 g of silver nitrate was added while mixing gently. This resulted in a slightly faint aqueous solution with a pH of around 1.7. To this solution, 0.7 g of glutamic acid was added and gently mixed. The silver(I)-tartaric acid coordination complex wherein glutamic acid is used to enhance silver coordination is referred to herein by title name "KB-Ag(I)". (The coordination complex is the same coordination complex referred to by the name "T-Ag" in U.S. Provisional Patent Application No. 60/642,805, but glutamic acid was added to the solution.) By using a micropipette, 25.4 µL of this solution was added to 10 mL of phosphate buffered saline (PBS). This resulted in an initial silver concentration of 250 µg/mL, confirmed by atomic absorption.

Results

Figure 2:
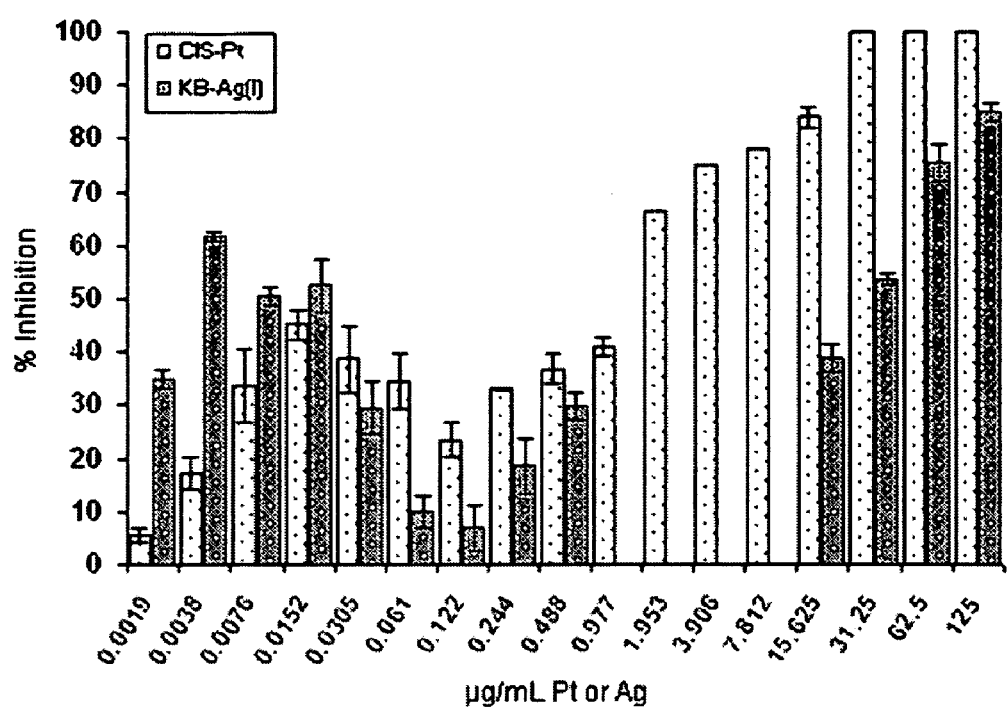
FIG. 2 is a chart illustrating the % inhibition of cisplatin (CIS-Pt) and silver (I) complex (KB-Ag(I)) for Jurkat.

I. Anticancer Activities:

The results obtained on cytotoxicity are depicted in FIGS. 1 and 2. The terms "CIS-Pt" and "KB-Ag(I)" refer to cisplatin and silver (I) coordination complex, respectively. For quantitative purposes, the results are expressed in terms of the amounts in µg/mL of Pt and Ag.

Careful examination of the data of FIGS. 1 and 2 on KB-Ag(I) reveals that the salient features of inhibition for T-47D and Jurkat are similar in that both profiles are triphasic. In general, Phase I is characterized by cytotoxicity in the nanoconcentration range, Phase II is characterized by the absence of cytotoxicity in the intermediate range, and finally Phase III is characterized by cytotoxicity in the microconcentration range. This behavior is more pronounced for T-47D in comparison with that of Jurkat, especially when compared to CIS-Pt. These phases occur abruptly as the concentration of KB-Ag(I) increases. For the range of concentrations studied here, the initiation of these phases is different for each tumor cell line examined. In the case of T-47D, the ranges of concentrations for Phases I, II, and III are 0.0019-0.0305, 0.061-7.812 and 15.625-125 µg/mL, respectively, while for Jurkat, the ranges are 0.0019-0.488, 0.977-7.812 and 15.625-125 µg/mL, respectively. It is of significance to observe here that the onset of cytotoxicity of Phase III is the same for both cell lines studied (15.625 µg/mL), inferring that the same mechanism responsible for this behavior is the same for solid and disseminated tumors as will be seen later. For both cell lines examined, Phase II might be considered a region where KB-Ag(I) is not toxic anymore at these concentrations. This finding could be interpreted in terms of KB-Ag(I) lacks of cytotoxicity, signaling cell redifferentiation where cells might have reverted back to becoming nonmalignant.

Throughout the concentration range studied, the results show that solid tumor cell line T-47D requires higher concentrations of KB-Ag(I) for inhibition in comparison with that for Jurkat, which is easily inhibited at lower concentrations. This behavior is also observed for CIS-Pt, but the inhibition of T-47D with CIS-Pt ceases with further dilutions, contrary to that of Jurkat, which continues with further dilutions (FIGS. 1 and 2). It may be noted here that at the same level of concentrations of Pt and Ag, CIS-Pt gives better cytotoxicity than KB-Ag(I), until the concentrations of both Pt and Ag are in the nano range where the % inhibition profile of KB-Ag(I) shifts and significantly improves, especially for T-47D (no cytotoxicity is observed for CIS-Pt in Phase I, FIG. 1).

The salient feature of the profile on KB-Ag(I) for T-47D is that the profile repeats itself in Phases I and III, starting at lower cytotoxicity and increasing as the concentration increases, while for Jurkat the profile in Phase I mimics that of Phase III until a concentration of 0.122 m/mL, and then shifts to become a bell-shaped curve (FIGS. 1 and 2). In the case of CIS-Pt, cytotoxicity continues to be present even at very low concentrations, until it loses its cytotoxicity for T-47D (FIG. 1).

A quantitative comparison between KB-Ag(I) and CIS-Pt in the range of 0.0019-0.0152 µg/mL (1.9-15.2 ng/mL) of FIGS. 1 and 2 reveals that within this region the average % inhibition of KB-Ag(I) is 2-fold larger than that for CIS-Pt on Jurkat (compare 49.9 with 25.4%) while for T-47D, the % inhibition for KB-Ag(I) is 38.3% compared with 0% for CIS-Pt. It is important to note here that for Jurkat, as the concentration of KB-Ag(I) and CIS-Pt decreases, the difference in cytotoxicity becomes more pronounced for the former in comparison with the latter.

To give a more quantitative pharmacokinetic-pharmacodynamic predictor regarding the activities of CIS-Pt and KB-Ag(I) of FIGS. 1 and 2, the ratio of the area-under-the-concentration-curve for the time period over 24 h ($AUC_{t>24}$) to the 50% maximal inhibitory concentration ($MIC_{50}$) was calculated ($AUC_{t>24}/MIC_{50}$), and the results are given in Table 1. The linear trapezoidal rule was used to calculate the $AUC_{t>24}$ values for both drugs, while the 50% maximal response produced by both CIS-Pt and KB-Ag(I) was read off the % inhibition-concentration curves (FIGS. 1 and 2). Notice here that for KB-Ag(I) there were two $MIC_{50}$ for both cell lines for Phases I and III. Regression models were applied to the data to assess the correlation between % inhibition and concentration. Multiple curve estimation procedure was employed, and the relative fit for each model was determined on the basis of the values of the correlation coefficient, $r^2$; the fit that gives $r^2$ values closer to 1.0 was selected. The regression equations were then integrated over the concentration intervals for each phase, and their sum was taken as the $AUC_{t>24}$.

The calculated $AUC_{t>24}$ values for T-47D for Phases I, II and III for CIS-Pt and KB-Ag(I) are 0.0, 2.05 and 107, and 0.0129, 0.0 and 59.4 cfu·µg/mL, respectively, while for Jurkat are 0.159, 4.89 and 108.1, and 0.0989, 0.0 and 77.6 cfu·µg/mL, respectively. The corresponding $MIC_{50}$ values for T-47D for CIS-Pt is 12.4 µg/mL, and for KB-Ag(I) are 0.025 (Phase I) and 50 µg/mL (Phase III), while for Jurkat for CIS-Pt is 1.28 µg/mL, and for KB-Ag(I) are 0.0076 (Phase I) and 27.4 µg/mL (Phase III).

TABLE 1

Calculated ratio of $AUC_{t>24}/MIC_{50}$ for CIS-Pt and KB-Ag(I) for the three phases.

| | Phases | | |
|---|---|---|---|
| | I | II | III |
| T-47D | | | |
| CIS-Pt | 0.0 | 0.165 | 8.63 |
| KB-Ag(I) | 0.516 | 0.0 | 1.19 |
| Jurkat | | | |
| CIS-Pt | 0.124 | 3.82 | 84.4 |
| KB-Ag(I) | 13.0 | 0.0 | 2.83 |

By comparing the values given in Table 1, the same conclusion can be deduced regarding the activities of these two drugs. As expected, CIS-Pt chemotherapeutic activity is better than that of KB-Ag(I) in Phases II and III, while the opposite holds true for Phase I. By calculating the ratio of activities of KB-Ag(I) to that of CIS-Pt for T-47D in Phases I, II and III, one would obtain the values of ∞, 0 and 0.138, respectively, while the values for Jurkat are 104.8, 0 and 0.0335, respectively. By examining these data, it can be concluded that KB-Ag(I) has significant activities on solid T-47D tumor in comparison with disseminated Jurkat tumor with respect to CIS-Pt. This might be attributed in turn to KB-Ag(I)'s ease of diffusion, which is related to its structural properties. It is of interest to note here that if the $AUC_{t>24}/MIC_{50}$ values of Table 1 for KB-Ag(I) and CIS-Pt for both tumor cell lines are added for Phases I and II where the concentrations of both Ag and Pt are within the range of interest for the systemic treatment of cancer, the values for KB-Ag(I) are almost 3.3-fold larger than the values for CIS-Pt (compare 0.516 with 0.165 for T-47D, and 13.0 with 3.94 for Jurkat). Even though KB-Ag(I) did not show any chemotherapeutic activities in Phase II, it is still superior to CIS-Pt at the lower-end of the metal concentration spectrum.

Accordingly, the cytotoxicity of KB-Ag(I) is superior to that of CIS-Pt, especially for T-47D solid tumor cell line, and for both tumor cell lines at very low metal concentrations. Considering the fact that silver has a much safer tolerance record than platinum, and exhibits better cytotoxic activities, especially at lower concentrations, as dictated by the present results, it would be advantageous and beneficial to substitute platinum complexes such as cisplatin with silver complexes according to the present invention.

II. Mechanism of Cytotoxicity:

Living cells can die by either necrosis "cell murder" or apoptosis "cell suicide". Necrosis occurs through an external damage, and is characterized by swollen morphology, lyses of plasma membrane, inflammation and tissue destruction, occurs within seconds, and can be induced by an overdose of cytotoxic agents ((Darzynkiewicz, Z., et al., *Hum. Cell*, 1, 3 (1998); Ferreira, C., et al., *Clin. Cancer Res.*, 8, 2024 (2002)). Apoptosis, on the other hand, is a genetically controlled coded autodigestion of living cells and is important in development and tissue homeostasis. It is characterized by a slow-irreversible biochemical processes through the activation of initiators or specific series of cytoplasmic proteases, leading cells to a no-return commitment to death. This process occurs when the genetic checkpoints of the cell cycle machinery is compromised, resulting in shrinkage of cells, membrane blebbing, degradation of chromatin and its dissolution (karyolysis), nuclear condensation, internucleosomal DNA fragmentation, mitochondrial break-down with the release of cytochrome c, which is a pivotal in the activation of the caspase cascade, and cytoskeletal cell disruption and breakage into small, membrane-wrapped, fragments ((Darzynkiewicz, Z., et al., *Hum. Cell*, 1, 3 (1998); Ferreira, C., et al., *Clin. Cancer Res.*, 8, 2024 (2002)). Since apoptosis is a gene-controlled event, it is susceptible to disruption by mutation, leading to many pathological conditions such as viral infections and cancer (Hengartner, M. O., *Nat.* 407, 770 (2002)). It is well established that chemotherapeutic drugs induce cytotoxic activities through a number of mechanisms, including necrosis (cytotoxic agents overdose), apoptosis, genotoxin (DNA damage), cell membrane damage, or free radical formation.

To examine the mode of inherent chemotherapeutic activities of silver (I) complexes, apoptosis was detected by the TUNEL assay for each cell line studies for Phases I, II and III identified above. Three concentrations, one for each phase, were chosen for the apoptotic studies for both the silver (I) complex and cisplatin, and compared with the controls. The concentrations chosen were 0.0076, 3.906, and 15.625 µg/mL for Phases I, II and III, respectively. The TUNEL assay results after 18 hours of incubation for T-47D and 6 hours for Jurkat are shown in FIGS. 3A-3H and 4A-4H. The 18 and 6-hour incubation periods were chosen because it was determined in previous experiments of this work that induction of apoptosis of silver (I) complex was within these times for these two cell lines.

Figures 3A, 3B, 3C, 3D, 3E, 3F, 3G, 3H:
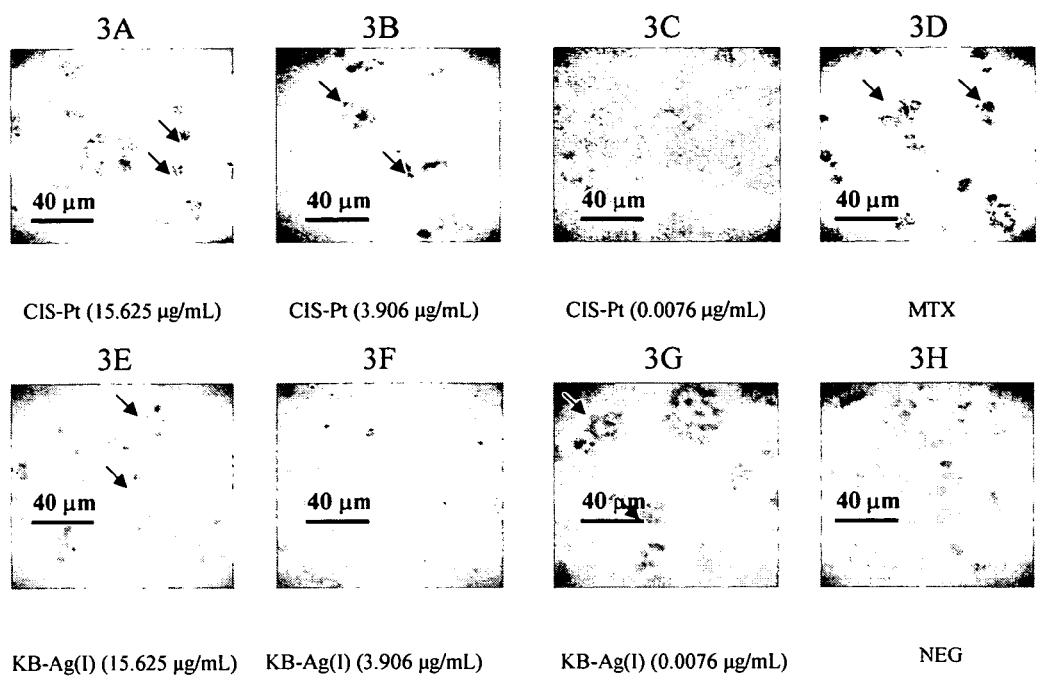
FIGS. 3A-3H depict photomicrographs showing in-situ apoptotic staining shown by arrows in T-47D. T-47D cells were treated with cisplatin (CIS-Pt) and silver (I) complex (KB-Ag(I)) to induce apoptosis at three different concentrations, 0.0076, 3.906, and 15.625 µg/mL. Positive and negative controls were used by using methotrexate (MTX) and by keeping the cells in the media without any cytotoxic drugs (NEG). Detection of apoptosis was performed by the Dead-End Colorimetric TUNEL (terminal deoxynucleotidyltransferase nick end labeling) assay for the detection of apoptosis in cultured cells as described in Promega kit.
Figures 4A, 4B, 4C, 4D, 4E, 4F, 4G, 4H:
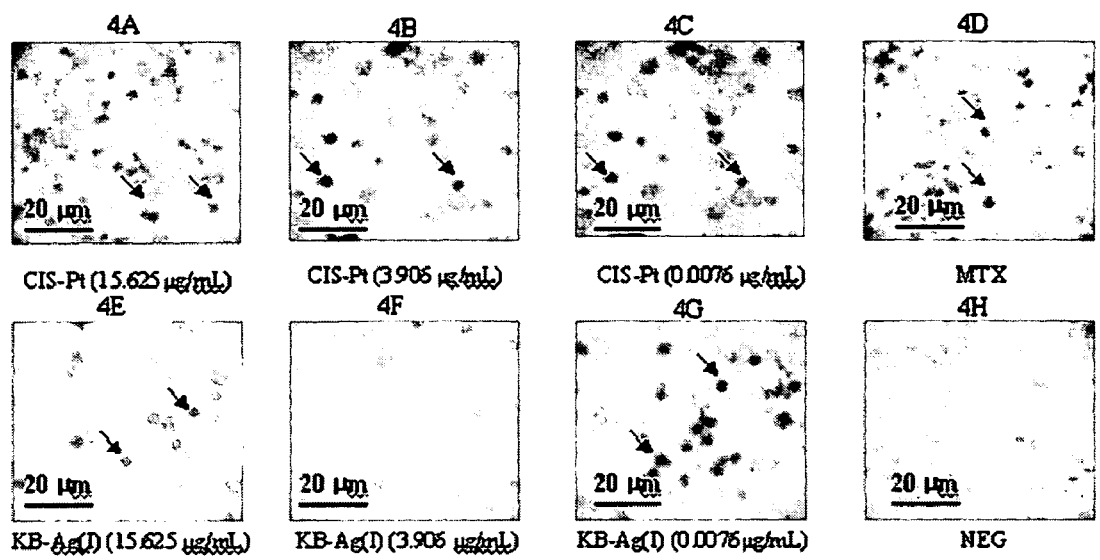
FIGS. 4A-4H depict photomicrographs showing in-situ apoptotic staining depicted by arrows in Jurkat. Jurkat cells were treated with cisplatin (CIS-Pt) and silver (I) complex (KB-Ag(I)) to induce apoptosis at three different concentrations, 0.0076, 3.906, and 15.625 μg/mL. Positive and negative controls were used by using methotrexate (MTX) and by keeping the cells in the media without any cytotoxic drugs (NEG). Detection of apoptosis was performed by the Dead-End Colorimetric TUNEL (terminal deoxynucleotidyltransferase nick end labeling) assay for the detection of apoptosis in cultured cells as described in Promega kit.

For both cell lines studied, it can be concluded from FIGS. 3 and 4 that apoptotic staining, depicted by arrows, is evident for both KB-Ag(I) and CIS-Pt at these concentrations. As can be seen, there are apparent alterations in cell morphology and detachment from the culture surface and cells became sparse and rounded. Cell shrinkage and internucleosomal DNA fragmentation are classical characteristics of apoptosis and not necrosis. However, in Phase II for both T-47D and Jurkat treated with KB-Ag(I) (FIGS. 3F and 4F, respectively,) apoptosis is absent, resembling that of the negatives (NEG) for both cell lines (FIGS. 3H and 4H, respectively), which corroborates the previous results, that is, the lack of cytotoxicity of KB-Ag(I) in this phase (FIGS. 1 and 2). For Jurkat treated with CIS-Pt, apoptosis is evident for the three concentrations studied (FIGS. 4A, 4B and 4C, respectively), while for T-47D apoptosis is absent at the lowest concentration studied (0.0076 µg/mL Pt) (FIG. 3C), again corroborating the previous results of FIGS. 1 and 2. It is also of significance to note here that the frequency of apoptosis is also reflected in the % inhibition results. For example, in the case of Jurkat treated with KB-Ag(I), the concentration at 0.0076 µg/mL of Ag corresponds to higher inhibition than that at 15.625 µg/mL of Ag (FIG. 2; compare 50.5% with 38.9%), which is fingerprinted in the apoptosis results (FIGS. 4E and 4G).

EXAMPLE 2

Preparation of Silver (I) Coordination Complex (KB'-Ag(I))

In order to examine the effect of the addition of amino acid, the same procedure was repeated as in Example 1, but no glutamic acid was added. A comparison of cytotoxic activity with respect to Jurkat cells is presented in FIG. 5. Here, KB'-Ag(I) refers to the silver(I)-tartaric acid coordination complex that is prepared without the addition of glutamic acid. (This coordination complex is the same as the coordination complex designated as T-Ag in U.S. Provisional Patent Application No. 60/642,805.) It can be seen that KB'-Ag(I) gives better cytotoxic activities than KB-Ag(I) until the concentration of Ag drops to 3.906 µg/mL, where its activity decreases, and the activity of KB-Ag(I) becomes superior. It can therefore be concluded that the addition of an amino acid in the preparation of a coordination complex of a cytotoxic metal and a chiral α-organic acid of the present invention, such as the silver(I)-tartaric acid coordination complex described herein causes the anticancer activities of the complex to profoundly increase at lower concentrations. It is noteworthy to mention here that a free silver ion solution was also prepared in an effort to examine its cytotoxic activities, and compare the results to those of KB-Ag(I) and KB'-Ag(I). This free silver ion solution was prepared in exactly the same way as in Examples 1 and 2 above, but no sodium tripolyphosphate, tartaric acid or glutamic acid was added to the solution. On the average, it was found that both KB-Ag(I) and KB'-Ag(I) induced one order of magnitude reduction of the original cell count on both T-47D and Jurkat when compared with the free silver ion solution, and below 15.625 µg/mL, the free silver ion solution did not exhibit any cytotoxic activities.

III. Preparation for KB-Ag(I) and KB'-Ag(I) Crystals:

Crystals of KB-Ag(I) or KB'-Ag(I) were prepared by the same procedure as described in Examples 1 and 2 above, but the mixture was allowed to stand for 24 hours at ambient temperature in the dark where crystals were formed. The mixture was then filtered vacuum, and the crystals were collected. This resulted in clear colorless single crystals of KB-Ag(I) and KB'-Ag(I).

Figure 5:
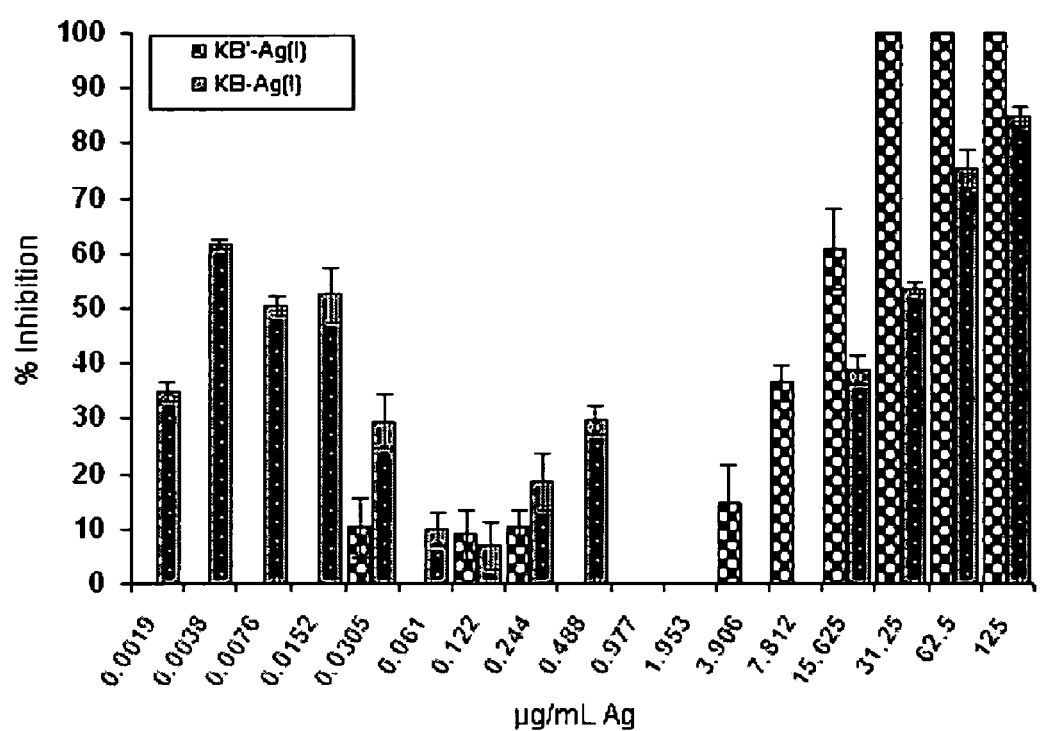
FIG. 5 is a chart illustrating the % inhibition of silver (I) complex with the addition of glutamic acid (KB-Ag(I)) and without (KB'-Ag(I)) for Jurkat.

IV. Molecular Structure, Thermal and Thermogravimetric Properties and Purity of KB-Ag(I) or KB'-Ag(I):

It is noteworthy to mention here that the molecular structure, thermal and thermogravimetric analyses for both KB-Ag(I) and KB'-Ag(I) were found to be the same except for the cytotoxic activities, being higher for the former at lower silver concentrations (FIG. 5). Hence, the foregoing discussion refers only to the silver (I) complex by KB-Ag(I).

I. Molecular Structure of KB-Ag(I)

Figure 6A:
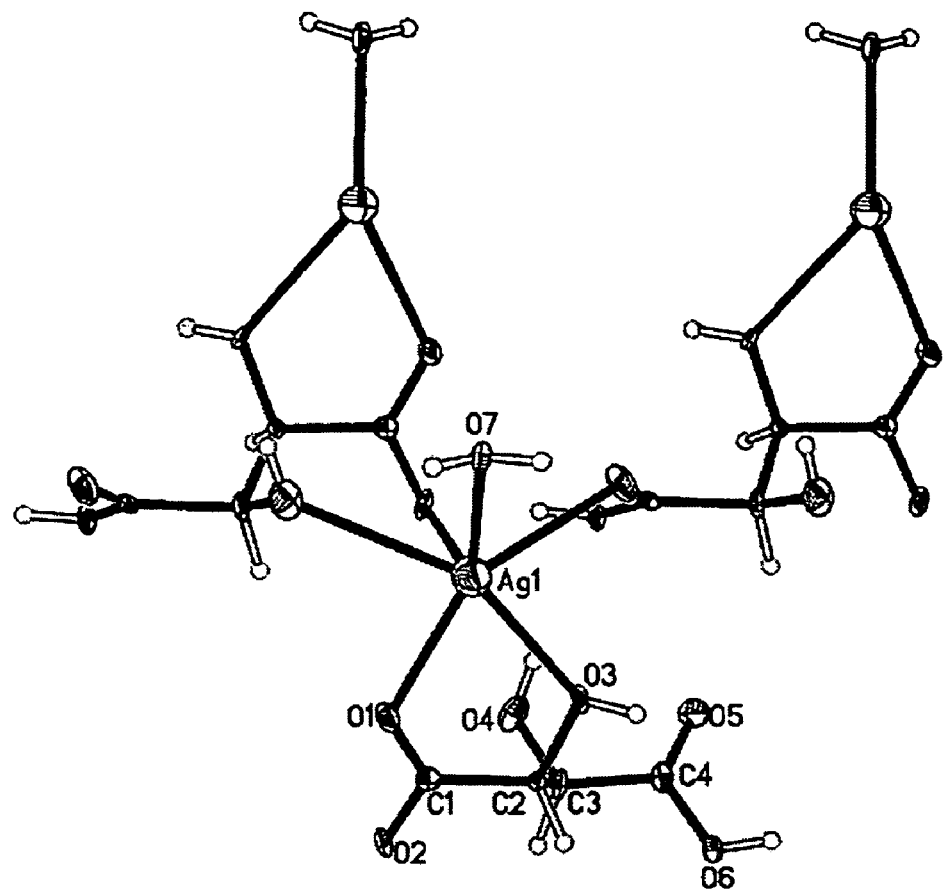
FIG. 6A depicts the molecular structure of the complex KB-Ag(I) or KB'-Ag(I) as determined by X-ray Crystallography.
Figure 6B:
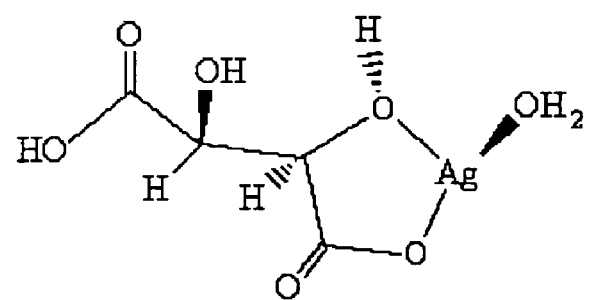
FIG. 6B is the structural formula of the complex KB-Ag(I) or KB'-Ag(I), represented stoichiometrically.

A view of the title compound KB-Ag(I) including the scheme of atomic numbering is given in FIGS. 6A and 6B. As depicted by FIG. 6A, the coordination sphere of the crystalline state of KB-Ag(I) shows a polymeric chain hydrate structure, and is constructed from silver complex molecules and water solvent molecules, with no imposed symmetry on it. The stereochemical structure of the title compound is basically a two-bidentate and two-unidentate chelate residue of tartrate rings and water, $[Ag(bidentate)_2(unidentate)_2]^{\pm}$. The water molecule is present stoichiometrically with respect to the complex, which is coordinated to the silver atom, as shown in FIG. 6B. The central silver atom is six-coordinated to six ligand donor oxygen atoms to form a distorted skew trapezoidal bipyramidal six-coordinate geometry, with two hydroxyloxygen donors and three carboxylate oxygen donors all from tartrate residue and one oxygen donor from $H_2O$. The tartaric acid residue coordinates to the Ag(1) center, forming 5-member and 6-member coordination rings. The 5-member ring complexation is one carboxylate oxygen (O1, off of C1) and one hydroxyloxygen (O3, off of C2), while the 6-member ring complexation is one carboxylate oxygen (O2, off of C1) and one hydroxyloxygen (O4, off of C3), and the remaining carboxylate (O5 and O6 off of C4) is not complexed to silver but is involved in the hydrogen bond between adjacent ligand molecules (see FIG. 7). The distances of Ag(1)-O(1) and Ag(1)-O(3) are not equivalent, being 2.356(3) and 2.489(3) Å, respectively. However, the distance of the bond between Ag and the water oxygen, Ag(1)-O(7), is nearly equivalent to that of Ag(1)-O(1), being 2.361(4) Å.

Figure 7:
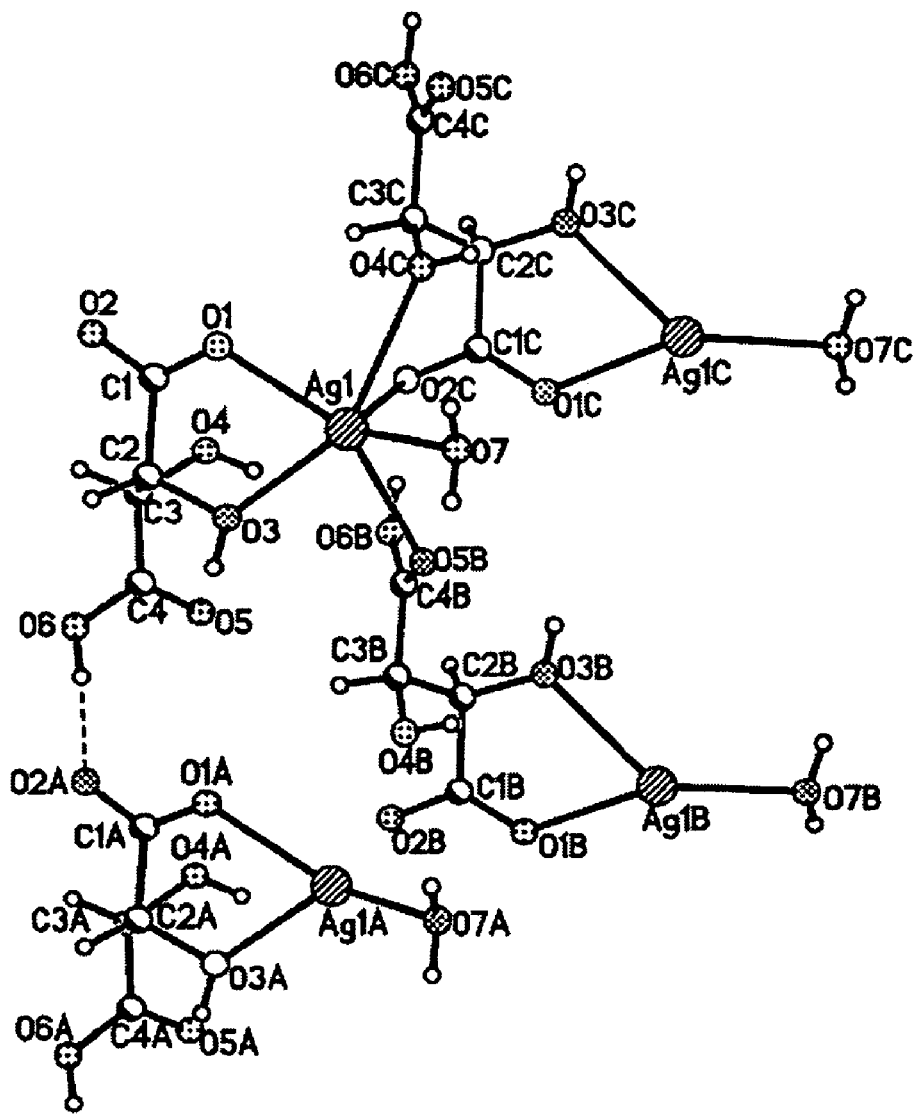
FIG. 7 depicts the environment of the Ag and H bonding of the carboxyl H (O6-H6 . . . O2A) for the complex KB-Ag(I) or KB'-Ag(I).

The Ag-O6 distance is 2.853 Å and so is considered outside of a typical coordination distance. To explain this behavior, FIG. 7 depicts the nature of the environment of Ag and H bonding of the carboxyl H (O6-H6 . . . O2A). A quasi-one dimensional chain structure is formed through O6-H6 . . . O2A hydrogen bonds in which the hydrogen H6 of the carboxylate links the adjacent complex through the carboxylate $O_2A$, broken line in FIG. 7. The O6-O2A distance is 2.537 Å, which supports the contention that O6 is not a part of the coordination sphere of the silver center. The angles O6-Ag-Ox, where x=1, 2, 3, 4, 5 and 7 are 87.7, 171.1, 87.3, 106.3, 111.6 and 69.2°, respectively.

A Cambridge Structural Database (CSD) search for possible matches was performed, and the results suggest that the molecular structure of KB-Ag(I) appears to match a previously published complex (Bott, R., et al., *Zeitschrift Für Kristallographie*, 209, 803 (1994)), including values of bond angles and lengths. A comprehensive structural data, including detailed crystal data, structure refinement, anisotropic parameters, bond distances and angles for the title compound KB-Ag(I) are given in Tables 2-7, below. What is of interest to note here is the fact that in the cited work the experimental conditions and the method in which the complex of the cited work was prepared are different than the ones presented by this invention, including the pH, the chemical milieu of the solution and the sequence of addition of chemicals, or the preparation steps. The complex in the cited work is prepared in water, while the complex of the present invention is prepared in phosphoric acid solution under highly acidic conditions, pH<2.0. Also, the chemical constituents are different: in the cited work only silver nitrate and tartaric acid are used, while in this invention, in addition to silver nitrate and tartaric acid, phosphoric acid and sodium tripolyphosphate were also included. It is also noteworthy to mention here that the crystals' shape as described in the cited work and the shape of the present crystals are different, being prismatic needles (0.26× 0.18×0.12 mm$^3$) for the former, and prisms for the latter (0.23×0.2×0.18 mm$^3$). Hence, it is of interest and attractive to note here that aside from the present complex KB-Ag(I) to be a novel anticancer drug, the present invention provides a new method for the preparation of this coordination complex.

TABLE 2

Crystal Data and Structure Refinement for the Title Compound KB—Ag(I).

| | |
|---|---|
| Empirical formula | $C_4H_7AgO_7$ |
| Formula weight | 274.97 |
| Temperature (K) | 170 ± 2 |
| $\lambda_{Mo-K\alpha}$ (Å) | 0.71073 |
| Crystal size (mm) | 0.23 × 0.2 × 0.18 |

TABLE 2-continued

Crystal Data and Structure Refinement for the Title Compound KB—Ag(I).

| | |
|---|---|
| Crystal system | Monoclinic |
| Space group | $P2_1$ |
| Unit cell dimension | |
| a (Å) | 5.98570(10) |
| b (Å) | 8.43390(10) |
| c (Å) | 7.24960(10) |
| α (°) | 90 |
| β (°) | 110.602(1) |
| γ (°) | 90 |
| Volume (Å$^3$) | 342.574(8) |
| Z | 2 |
| $\rho_{calcd}$ (g/cm$^3$) | 2.666 |
| Absorption coefficient (mm$^{-1}$) | 2.941 |
| F(000) | 268 |
| Theta range for data collection (°) | 3.00 to 28.29 |
| Index ranges | $-7 \leq 7, -11 \leq k \leq 11, -9 \leq 1 \leq 9$ |
| Reflections collected | 6550 |
| Independent reflections | 1685 [R(int) = 0.025] |
| Completeness to theta = 28.29° | 99.4% |
| Absorption correction | Semi-empirical from equivalents |
| Max. and min. transmission | 0.6196 and 0.5511 |
| Refinement method | Full-matrix least-squares on F$^2$ |
| Data/restraints/parameters | 1685/1/109 |
| Goodness-of-fit on F$^2$ | 1.134 |
| Final R indices [I > 2sigma(I)] | R1 = 0.0287, wR2 = 0.0872 |
| R indices (all data) | R1 = 0.0291, wR2 = 0.0875 |
| Absolute structure parameter | 0.05(5) |
| Largest diff. Peak and hole (e · Å$^{-3}$) | 0.748 and −0.819 |

TABLE 3

Atomic coordinates (×10$^4$) and equivalent isotropic displacement parameters (Å$^2$ × 10$^3$) for the title compound KB—Ag(I).

| | x | y | z | U*(eq) |
|---|---|---|---|---|
| Ag(1) | −2118(1) | −2506(1) | −3232(1) | 18(1) |
| O(1) | −2257(7) | −7(4) | −4721(5) | 11(1) |
| O(2) | −3014(5) | 2565(7) | −4865(4) | 9(1) |
| O(3) | −2294(6) | −255(4) | −1066(5) | 8(1) |
| O(4) | −6790(6) | 1460(5) | −3076(5) | 13(1) |
| O(5) | −6280(6) | 1335(4) | 724(5) | 12(1) |
| O(6) | −2950(6) | 2811(3) | 1666(5) | 8(1) |
| O(7) | −256(6) | −5015(4) | −2801(5) | 9(1) |
| C(1) | −2590(8) | 1254(5) | −3983(6) | 6(1) |
| C(2) | −2464(8) | 1300(5) | −1824(6) | 5(1) |
| C(3) | −4691(8) | 2145(5) | −1721(6) | 7(1) |
| C(4) | −4733(8) | 2064(5) | 356(7) | 6(1) |

U*(eq) is defined as one third of the trace of the orthogonal U$^{ij}$ tensor.

TABLE 4

Bond length (Å) and angles (°) of the Title Compound KB—Ag(I).

| | |
|---|---|
| Ag(1)—O(1) | 2.356(3) |
| Ag(1)—O(7) | 2.361(4) |
| Ag(1)—O(3) | 2.489(3) |
| Ag(1)—O(5)#1 | 2.531(3) |
| O(1)—C(1) | 1.237(6) |
| O(2)—C(1) | 1.258(7) |
| O(3)—C(2) | 1.412(5) |
| O(4)—C(3) | 1.417(5) |
| O(5)—C(4) | 1.216(6) |
| O(5)—Ag(1)#2 | 2.531(3) |
| O(6)—C(4) | 1.313(6) |
| C(1)—C(2) | 1.541(6) |
| C(2)—C(3) | 1.536(6) |
| C(3)—C(4) | 1.517(6) |
| O(1)—Ag(1)—O(7) | 143.27(12) |
| O(1)—Ag(1)—O(3) | 66.69(11) |
| O(7)—Ag(1)—O(3) | 136.29(11) |

TABLE 4-continued

Bond length (Å) and angles (°) of the Title Compound KB—Ag(I).

| | |
|---|---|
| O(1)—Ag(1)—O(5)#1 | 135.50(12) |
| O(7)—Ag(1)—O(5)#1 | 80.75(12) |
| O(3)—Ag(1)—O(5)#1 | 74.37(11) |
| C(1)—O(1)—Ag(1) | 123.80(3) |
| C(2)—O(3)—Ag(1) | 118.40(3) |
| C(4)—O(5)—Ag(1)#2 | 118.20(3) |
| O(1)—C(1)—O(2) | 124.80(4) |
| O(1)—C(1)—C(2) | 120.20(4) |
| O(2)—C(1)—C(2) | 115.00(4) |
| O(3)—C(2)—C(3) | 110.90(4) |
| O(3)—C(2)—C(1) | 110.10(4) |
| C(3)—C(2)—C(1) | 109.20(3) |
| O(4)—C(3)—C(4) | 110.40(4) |
| O(4)—C(3)—C(2) | 110.50(3) |
| C(4)—C(3)—C(2) | 110.20(3) |
| O(5)—C(4)—O(6) | 124.90(4) |
| O(5)—C(4)—C(3) | 121.40(4) |
| O(6)—C(4)—C(3) | 113.80(4) |

Symmetry transformations used to generate equivalent atoms. #1: −x − 1, y − ½, −z; and #2: −x − 1, y + ½, −z.

TABLE 5

Anisotropic displacement parameters (Å² × 10³) for the title compound KB—Ag(I).

| | $U^{11}$ | $U^{22}$ | $U^{33}$ | $U^{23}$ | $U^{13}$ | $U^{12}$ |
|---|---|---|---|---|---|---|
| Ag(1) | 23(1) | 16(1) | 19(1) | 1(1) | 9(1) | 2(1) |
| O(1) | 21(2) | 7(1) | 10(2) | 0(1) | 11(1) | 0(1) |
| O(2) | 15(1) | 9(1) | 4(1) | 2(1) | 4(1) | −1(2) |
| O(3) | 15(2) | 5(1) | 3(1) | 2(1) | 2(1) | 2(1) |
| O(4) | 10(2) | 18(2) | 9(2) | −3(1) | −1(1) | 0(1) |
| O(5) | 16(2) | 12(2) | 14(2) | −4(1) | 12(1) | −4(1) |
| O(6) | 10(1) | 9(2) | 5(1) | −1(1) | 5(1) | −1(1) |
| O(7) | 12(1) | 11(1) | 4(1) | 0(1) | 2(1) | −2(1) |
| C(1) | 5(2) | 13(2) | 4(2) | 0(2) | 5(2) | −2(2) |
| C(2) | 9(2) | 4(2) | 4(2) | 0(1) | 3(2) | −1(1) |
| C(3) | 7(2) | 11(2) | 2(2) | −1(1) | 2(1) | 1(1) |
| C(4) | 8(2) | 6(2) | 6(2) | 0(1) | 4(2) | 4(1) |

TABLE 6

Hydrogen coordinates (×10⁴) and isotropic displacement parameters (Å² × 10³) for the title compound KB—Ag(I).

| | x | y | z | U(eq) |
|---|---|---|---|---|
| H(3) | −1503 | −243 | 148 | 12 |
| H(4) | −6907 | 516 | −2753 | 20 |
| H(6) | −3040 | 2697 | 2789 | 11 |
| H(7A) | 578 | −5146 | −1590 | 13 |
| H(7B) | 633 | −5073 | −3490 | 13 |
| H(2A) | −1015 | 1911 | −1025 | 6 |
| H(3A) | −4625 | 3285 | −2080 | 8 |

TABLE 7

Torsion angles (°) of the title compound KB—Ag(I).

| | |
|---|---|
| O(7)—Ag(1)—O(1)—C(1) | 145.1(3) |
| O(3)—Ag(1)—O(1)—C(1) | −7.5(3) |
| O(5)#1—Ag(1)—O(1)—C(1) | 23.5(4) |
| O(1)—Ag(1)—O(3)—C(2) | 2.1(3) |
| O(7)—Ag(1)—O(3)—C(2) | 146.4(3) |
| O(5)#1—Ag(1)—O(3)—C(2) | −155.9(3) |
| Ag(1)—O(1)—C(1)—O(2) | −169.2(3) |
| Ag(1)—O(1)—C(1)—C(2) | 11.7(6) |
| Ag(1)—O(3)—C(2)—C(3) | 122.8(3) |
| Ag(1)—O(3)—C(2)—C(1) | 1.9(4) |
| O(1)—C(1)—C(2)—O(3) | −8.4(5) |

TABLE 7-continued

Torsion angles (°) of the title compound KB—Ag(I).

| | |
|---|---|
| O(2)—C(1)—C(2)—O(3) | 172.4(4) |
| O(1)—C(1)—C(2)—C(3) | −130.4(4) |
| O(2)—C(1)—C(2)—C(3) | 50.4(5) |
| O(3)—C(2)—C(3)—O(4) | 69.3(4) |
| C(1)—C(2)—C(3)—O(4) | 52.1(5) |
| O(3)—C(2)—C(3)—C(4) | 53.0(4) |
| C(1)—C(2)—C(3)—C(4) | 174.4(3) |
| Ag(1)#2—O(5)—C(4)—O(6) | 39.5(5) |
| Ag(1)#2—O(5)—C(4)—C(3) | −142.0(3) |
| O(4)—C(3)—C(4)—O(5) | 7.5(6) |
| C(2)—C(3)—C(4)—O(5) | −114.9(4) |
| O(4)—C(3)—C(4)—O(6) | −173.9(4) |
| C(2)—C(3)—C(4)—O(6) | 63.8(4) |

Symmetry transformations used to generate equivalent atoms. #1: −x − 1, y − ½, −z; and #2: −x − 1, y + ½, −z.

Some of the Ag—O bonds were outside the coordination sphere for which the software normally calculates bond length and angles. These values around the silver center were derived manually and are shown in Table 8, below. Some of these results are the same as those shown in Table 4.

TABLE 8

Selected bond length (Å) and angles (°) for the title compound KB—Ag(I).

| Ag—Ox | | Ligand Environment of Ag1 Angle Ox—Ag—Oy | | | | |
|---|---|---|---|---|---|---|
| Ligand | Length | O1 | O2 | O3 | O4 | O5 |
| O1 | 2.356 | | | | | |
| O2 | 2.751 | 83.7 | | | | |
| O3 | 2.489 | 66.7 | 91.6 | | | |
| O4 | 2.668 | 82.9 | 70.2 | 146.3 | | |
| O5 | 2.531 | 135.5 | 76.5 | 74.4 | 125.0 | |
| O7 | 2.361 | 143.3 | 117.0 | 136.3 | 77.1 | 80.7 |

II. Thermal and Thermogravimetric Analyses of KB-Ag(I)

Figure 8:
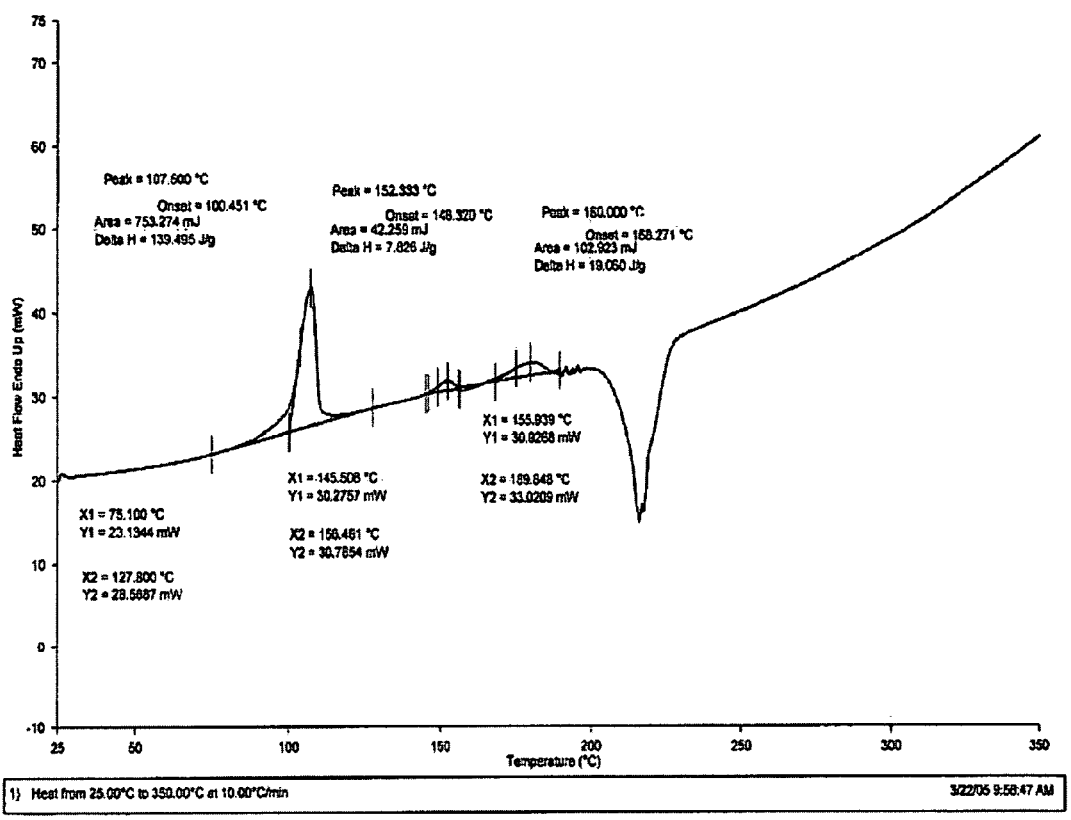
FIG. 8 is a graph showing the thermal results obtained on the complex KB-Ag(I) or KB'-Ag(I), scan temperature range 25-350° C. at a heating rate of 10° C./min.
Figure 9:
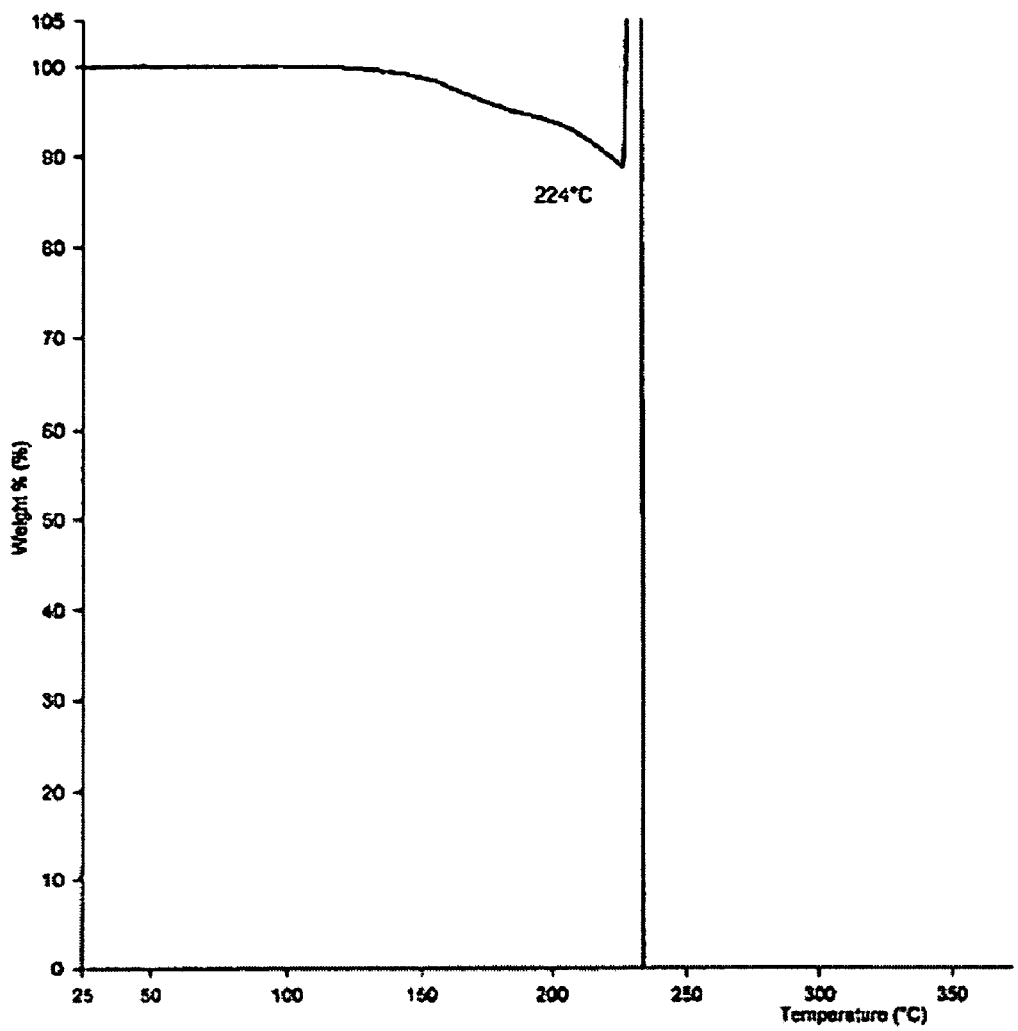
FIG. 9 is a graph showing the thermogravimetric results obtained on the complex KB-Ag(I) or KB'-Ag(I), scan temperature range of 25-600° C. at a heating rate of 20° C./min.

FIG. 8 shows the results of the DSC from 25 to 350° C. at a temperature program rate of 10° C./min on crystals of KB-Ag(I) with a sample weight of 5.4 mg, while FIG. 9 depicts the results of the TG data as a function of temperature with a sample weight of 11.872 mg. The profile of FIG. 8 depicts three endothermic bands and one exothermic band. The first endothermic band is between 100.451-120° C. with a peak at 107.5° C., the second is between 146.32-156.506° C. with a peak at 152.333° C., and finally the third is between 168.271-189.848° C. with a peak at 180° C., while the exothermic band is between 215.583-233° C. with a peak at 221.666° C. The final exothermic peak at 221.666° C. corresponds to thermal decomposition where the sample, seen in the DSC profile of FIG. 8, suddenly decomposes, expands and makes contact inside the instrument. Both the temperature range and the % weight loss (FIGS. 8 and 9) suggest that the high temperature phenomenon is indicative of decomposition of KB-Ag(I), and not melting.

The second endothermic peak at 152.333° of FIG. 8 can be attributed to dehydration of the molecular water attached to the silver atom (FIG. 6):

This slow dehydration step (loss of mass) commences at approximately 130° C. and proceeds until about 150° C., and is accompanied by a weight loss (≈2%) as can be seen in FIG. 9. The third endothermic peak at 180° C. represents fusion with a % weight loss of about 3% and occurs approximately between 150°-195° C. (FIG. 9). The final exothermic peak at 221.666° C. corresponds to thermal decomposition. As can be seen by FIG. 9, thermal decomposition is observed at about 195° C., which is depicted by sharp profile with a rapid % weight loss (≈6%). As the sample approaches the decomposition temperature, seen in the DSC profile of FIG. 8, it suddenly decomposes, expands and makes contact inside the instrument. The present data suggest that KB-Ag(I) is stable up to around 145° C., and at higher temperature dehydration, fusion and decomposition begin.

III. Purity of KB-Ag(I)

The purity of KB-Ag(I) for carbon and hydrogen was determined by a combustion/gravimetric method using a Lindberg C/H elemental analyzer, while for silver standard atomic absorption was employed using a Perkin-Elmer PE 2100 AAS. The data obtained confirming the degree of purity of KB-Ag(I) for carbon and hydrogen are given in Table 9.

TABLE 9

Summary of experimental data confirming the purity of KB—Ag(I) ($C_4H_7AgO_7$).

| Element | Analysis Calculated | Analysis Found | Error |
|---|---|---|---|
| % Carbon | 17.47% | 17.77% | ±0.30% |
| % Hydrogen | 2.57% | 2.48% | ±0.17% |

Since the data agree with the calculated ones within ±0.4%, the elemental analyses are correct, and conform to the American Chemical Society (ACS) standards. The analysis found for silver was 38.22%, while the calculated one was 39.23% with an error of ±1.01%. This value is within the experimental error of the atomic absorption analytical method used to determine silver, which was ±1.7%.

FURTHER EXAMPLES

The cytotoxicity of other chiral α-organic acids such as D-tartaric acid, L-malic acid, and L-lactic acid has also been studied. The same procedure was repeated as in Example 1, but no glutamic acid was added. The amount of each acid added was in accordance with its molecular weight relative to the concentration of silver present in solution; the molar concentration of each acid added was the same as in the case of Example 1 or 2 above. The initial amount of silver added was the same for all runs, equaling that of Examples 1 and 2 above. Triplicate runs were performed for each concentration and for each acid, and the results are averaged and reported. The results of cytotoxicity with respect to Jurkat cells expressed in terms of % inhibition as a function of concentration are presented in Table 10, below. Here, D-TA, L-MA, and L-LA refer to D-tartaric acid, L-malic acid, and L-lactic acid, respectively. For comparative purposes, the results obtained on KB'-Ag(I), L-tartaric acid (L-TA) without glutamic acid—Example 2, are also shown. By examining the data of Table 10, it is interesting to note that the general trend of cytotoxicity for D-TA, L-MA and L-LA is the same as for KB'-Ag(I), that is, three phases of cytotoxicity are present as discussed earlier. However, the range of these phases is different for each acid examined, except for KB'-Ag(I) or L-TA and D-TA. It is also interesting to note that L-TA gives better cytotoxicity than D-TA. On the average, the order of cytotoxicity is L-MA>KB'-Ag(I) or L-TA>D-TA>L-LA.

TABLE 10

% Inhibition for KB'-Ag(I), D-TA, L-MA and L-LA.

| Concentration of Ag | % Inhibition | | | |
|---|---|---|---|---|
| (μg/mL) | KB'-Ag(I) | D-TA | L-MA | L-LA |
| 125 | 100 | 100 | 100 | 100 |
| 62.5 | 100 | 100 | 100 | 100 |
| 31.25 | 100 | 86.0 | 97.3 | 81.1 |
| 15.625 | 60.9 | 30.4 | 56.3 | 40.0 |
| 7.812 | 36.5 | 14.6 | 28.6 | 20.9 |
| 3.906 | 14.7 | 4.1 | 17.9 | 3.6 |
| 1.953 | 0.0 | 0.0 | 0.0 | 0.0 |
| 0.977 | 0.0 | 0.0 | 0.0 | 0.9 |
| 0.488 | 0.0 | 0.0 | 17.9 | 0.0 |
| 0.244 | 9.6 | 7.0 | 17.9 | 0.0 |
| 0.122 | 8.3 | 0.0 | 13.4 | 0.0 |
| 0.061 | 0.0 | 0.0 | 3.6 | 0.0 |
| 0.0305 | 9.6 | 0.0 | 0.0 | 0.0 |
| 0.0152 | 0.0 | 0.0 | 2.7 | 0.0 |
| 0.0076 | 0.0 | 0.0 | 0.0 | 0.0 |
| 0.0038 | 0.0 | 0.0 | 0.0 | 0.0 |
| 0.0019 | 0.0 | 0.0 | 0.0 | 0.0 |

ADDITIONAL REFERENCES

Batarseh, K. I., *J. Antimicrob. Chemo.*, 54, 546 (2004).
Bernes-Price, S. J. et al., *Coord. Chem. Rev.*, 185-186, 823 (1999).
Bernes-Price, S. J. et al., *J. Inorg. Biochem.*, 33, 285 (1988).
Bernes-Price, S. J. et al., *Inorg. Chem.*, 25, 596 (1986).

All publications, patents, and patent applications mentioned herein form a part of the patent application and are incorporated in their entirety by reference herein.

Applicant specifically incorporates the entire contents of all cited references in this disclosure. Further, when an amount, concentration, or other value or parameter is given as either a range, preferred range, or a list of upper preferable values and lower preferable values, this is to be understood as specifically disclosing all ranges formed from any pair of any upper range limit or preferred value and any lower range limit or preferred value, regardless of whether ranges are separately disclosed. Where a range of numerical values is recited herein, unless otherwise stated, the range is intended to include the endpoints thereof, and all integers and fractions within the range. It is not intended that the scope of the invention be limited to the specific values recited when defining a range.

The preceding discussion, examples, procedures, and specific salient features disclosed herein are solely intended for providing the general and certain preferred embodiments of the present invention. Thus, various modifications and suggestions in lieu thereof can be implemented by those skilled in the art. These should be an essential part of this application and can be made consistent with the letter and spirit of the foregoing disclosure, and within the true scope, merits and purview of this invention, which is presented by the following claims.

What is claimed is:

1. A method of making a composition that is cytotoxic or antineoplastic and comprising a metal coordination complex of a silver(I) chiral α-organic acid coordination complex in a pharmaceutical carrier, wherein the metal coordination complex is crystalline and coordinates to one silver atom, and the chiral α-organic acid is tartaric acid, malic acid, lactic acid or mixtures thereof, the method comprising the steps of:

(a) adding at least one inorganic acid to an aqueous solvent to provide a solution having a pH of 2.0 or less, then (b) adding at least one surfactant to the solution after step (a), then (c) adding at least one chiral α-organic acid to the solution after step (b), wherein the chiral α-organic acid is tartaric acid, malic acid, lactic acid or mixtures thereof, and then (d) adding at least one silver(I) salt to the solution after step (c), whereby the chiral α-organic acid and silver (I) from the silver(I) salt interact to form the silver(I) chiral α-organic acid complex.

2. The method of claim 1, wherein the amount of surfactant that is present in the aqueous solvent is no greater than an equimolar portion with respect to the amount of silver(I) present, and the amount of chiral α-organic acid that is present in the aqueous solvent is no greater than four times the equimolar portion with respect to the amount of silver(I) present.

3. The method of claim 2, wherein the surfactant is sodium tripolyphosphate and the inorganic acid is phosphoric acid.

4. The method of claim 2, wherein the chiral α-organic acid is tartaric acid.

5. The method of claim 2, further including a step (e) of adding at least one amino acid to the composition after step (d).

6. The method of claim 5, wherein the at least one amino acid is isoleucine, phenylalanine, leucine, lysine, methionine, threonine, tryptophan, valine, alanine, glycine, arginine, histidine, hydroxyproline, gamma-aminobutyric acid, asparagine, aspartic acid, cysteine, glutamic acid, glutamine, phenylalanine, proline, serine, tyrosine, or mixtures thereof.

7. A method of making a crystalline cytotoxic metal chiral α-organic acid coordination complex, comprising the steps of:

(a) adding at least one inorganic acid to an aqueous solvent to provide a solution having a pH of 2.0 or less, then (b) adding at least one surfactant to the solution after step (a), then (c) adding at least one chiral α-organic acid to the solution after step (b), wherein the chiral α-organic acid is tartaric acid, malic acid, lactic acid or mixtures thereof, and then (d) adding at least one cytotoxic metal to the solution after step (c), whereby the chiral α-organic acid and cytotoxic metal interact to form the cytotoxic metal chiral α-organic acid complex, wherein the complex coordinates to one metal atom.

8. The method of claim 5, wherein the at least one amino acid is glutamic acid.

9. The method of claim 1, further comprising adding at least one DNA-intercalating agent, at least one angiogenesis inhibitory agent, or both.

10. The method of claim 1, wherein the chiral α-organic acid is L-(+)-tartaric acid or (2R,3R)-(+)-tartaric acid.

11. The method of claim 1, wherein the silver (I) chiral α-organic acid complex comprises the formula $C_4H_7AgO_7$.

12. The method of claim 1, wherein the silver (I) chiral α-organic acid complex comprises the structure:

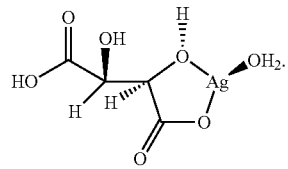

* * * * *